US 8,048,407 B2

(12) United States Patent
Vernon et al.

(10) Patent No.: US 8,048,407 B2
(45) Date of Patent: Nov. 1, 2011

(54) IN SITU GELLING SELF-REACTIVE MATERIALS FOR EMBOLIZATION

(76) Inventors: Brent Vernon, Mesa, AZ (US); Merrill Birdno, Durham, NC (US); Mark C. Preul, Scottsdale, AZ (US)

( * ) Notice: Subject to any disclaimer, the term of this patent is extended or adjusted under 35 U.S.C. 154(b) by 1366 days.

(21) Appl. No.: 10/554,046

(22) PCT Filed: Apr. 26, 2004

(86) PCT No.: PCT/US2004/013189
§ 371 (c)(1),
(2), (4) Date: Oct. 21, 2005

(87) PCT Pub. No.: WO2004/096152
PCT Pub. Date: Nov. 11, 2004

(65) Prior Publication Data
US 2006/0263301 A1    Nov. 23, 2006

Related U.S. Application Data

(60) Provisional application No. 60/465,376, filed on Apr. 24, 2003.

(51) Int. Cl.
A61K 31/74    (2006.01)
A61K 49/04    (2006.01)
A61K 31/765    (2006.01)

(52) U.S. Cl. ............... 424/78.08; 424/9.4; 424/78.31; 424/78.37

(58) Field of Classification Search ............... 424/9.4, 424/78.3, 78.31, 78.08, 78.37
See application file for complete search history.

(56) References Cited

U.S. PATENT DOCUMENTS

| 4,881,825 | A | 11/1989 | Olesen |
| 4,978,619 | A | 12/1990 | Kajiwara et al. |
| 5,356,432 | A | 10/1994 | Rutkow et al. |
| 5,514,379 | A | 5/1996 | Weissleder et al. |
| 5,667,767 | A * | 9/1997 | Greff et al. ............... 424/9.411 |
| 5,823,198 | A | 10/1998 | Jones et al. |
| 6,066,325 | A | 5/2000 | Wallace et al. |
| 6,096,021 | A | 8/2000 | Helm et al. |
| 6,113,629 | A | 9/2000 | Ken |
| 6,152,943 | A | 11/2000 | Sawhney |
| 6,165,193 | A | 12/2000 | Greene, Jr. et al. |
| 6,245,090 | B1 | 6/2001 | Gilson et al. |

(Continued)

FOREIGN PATENT DOCUMENTS
WO    WO2004/096152    11/2004

OTHER PUBLICATIONS

Vernon et al. ("Water-borne, in situ cross-linked biomaterials from phase-segregated precursors," in J. Biomed. Material Res., Mar. 1, 2003, 64(3), pp. 447-456).*

(Continued)

Primary Examiner — Blessing Fubara
(74) Attorney, Agent, or Firm — Maschoff Gilmore & Israelsen

(57) ABSTRACT

A method and composition for treating arteriovenous malformations (AVMs), or abnormal vasculature in the body are provided. The method comprises introducing into the region of an AVM a composition comprising a nucleophilic component, such as a thiol, and a component containing a conjugated unsaturated bond, such as an acrylate through a catheter, whereby the composition crosslinks within the body to block or occlude the AVM.

18 Claims, 9 Drawing Sheets

U.S. PATENT DOCUMENTS

| | | | |
|---|---|---|---|
| 6,299,619 | B1 | 10/2001 | Greene, Jr. et al. |
| 6,312,421 | B1 | 11/2001 | Boock |
| 6,342,202 | B1 | 1/2002 | Evans et al. |
| 6,428,576 | B1 * | 8/2002 | Haldimann ............... 623/17.16 |
| 6,463,317 | B1 | 10/2002 | Kuckarczyk et al. |
| 6,475,516 | B2 | 11/2002 | DiCosmo et al. |
| 6,645,167 | B1 * | 11/2003 | Whalen et al. ............... 604/28 |

OTHER PUBLICATIONS

Verduyn Lunel ("Significance of annulus fibrosus of heart in relation to AV conduction and ventricular activation in cases of Wolff-Parkinson-White syndrome," in British Heart Journal, 1972, 34, 1263-1271).*

Becker, T. et al., Calcium Alginate Gel: A biocompatible and mechanically stable polymer for endovascular treatment. Journal of Biomedical Materials Research, vol. 54 (2001), pp. 76-86.

Becker, T. et al., Flow properties of liquid calcium alginate polymer injected through medical microcatheters for endovascular embolization. Journal of Biomedical Materials Research, accepted Dec. 19, 2001, pp. 533-540.

Hillman, J., Population-based analysis of arteriovenous malformation treatment. J. Neurosurg. Oct. 2001: 95(4):633-637.

Irie, K. et al., Treatment of arteriovenous malformation of the brain—preliminary experience. J. Clin. Neurosci. Sep. 2000; 7 Supple 1:24-29.

Jizong, Z., et al., Combination of intraoperative embolisation with surgical resection for treatment of giant cerebal arteriovenous malformations. J. Clin. Neurosci. Sep. 2000; 7 Suppl. 1:54-59.

Li, Xiaowei, et al., Thermosensitive N-isopropylacrylamide—N-propylacrylamide-vinyl pyrrolidone terpolymers: Synthesis, characterization and preliminary application as embolic agents. J. Biomaterials 2005.05.094.

Liu, H.M., et al., Embolization of cerebral arteriovenous malformations with n-butyl-2-cyanoacrylate. J. Formos.Med. Addoc. Dec. 2000: 99(12):906-913.

Soga, Youji, M.D., et al., Calcium Alginate Provides a High ° of Embolization in Aneurysm Models: A Specific Comparison to Coil Packing, Neurosurgery, vol. 55, No. 6, Dec. 2004, pp. 1401-1409.

Vernon, B. et al., Water-borne, in-situ Cross-Linked Biomaterials from Phase Segregated Precursors, 2003 Wiley Periodicals, Inc. J Biomed Mater Res 64A: 447-456, 2003.

Wallace, R. et al., Brain Arteriovenous Malformations. Neuroimaging Clin. N. America. May 1998; 8(2): 383-99.

Wallace, R. et al., The Safety and Effectiveness of Brain AVM Embolization using Acrylic and Particles: The Experience of a Single Institution, Neurosurgery. Oct. 1995; 37(4): 606-18.

Wuyts FL, Vanhuyse VJ, Langewouters GJ, Decraemer WF, Raman ER, Buyle S. Elastic properties of human aortas in relation to age and atherosclerosis: a structural model. Phys Med Biol. Oct. 1995; 40(10):1577-97.

Zhao, Chengru, et al., A new thermosensitive polymer as nonadhesive liquid embolism material, Current Applied Physics, 5 (2005), 497-500.

* cited by examiner

CA

IN SITU GELLING SELF-REACTIVE MATERIALS FOR EMBOLIZATION

CROSS-REFERENCE TO RELATED APPLICATION(S)

This application claims priority to U.S. Provisional Application No. 60/465,376, filed Apr. 24, 2003, the disclosure of which is incorporated herein by reference.

FIELD OF THE INVENTION

The present invention is directed to an in situ occluding gelling material for use in embolization medical treatments, more particularly the current invention is directed to gelling materials consisting of a nucleophilic component and a component containing a conjugated unsaturated bond, which can be used to occlude or block arteriovenous malformations (AVMs), or abnormal vasculature in the body.

BACKGROUND OF THE INVENTION

Arteriovenous malformations (AVMs) are defects of the circulatory system that are generally believed to arise during embryonic or fetal development or soon after birth. They are comprised of snarled tangles of arteries and veins. The presence of an AVM disrupts the flow of blood through the body. Although AVMs can develop in many different sites, those located in the brain or spinal cord can have especially widespread effects on the body. AVMs of the brain or spinal cord (neurological AVMs) are believed to affect approximately 300,000 Americans. They occur in males and females of all racial or ethnic backgrounds at roughly equal rates.

Most people with neurological AVMs experience few, if any, significant symptoms, and the malformations tend to be discovered only incidentally, usually either at autopsy or during treatment for an unrelated disorder. But for about 12 percent of the affected population (about 36,000 of the estimated 300,000 Americans with AVMs), these abnormalities, also called lesions, cause symptoms that vary greatly in severity. For a small fraction of the individuals within this group, such symptoms are severe enough to become debilitating or even life-threatening. Each year about one percent of those with AVMs will die as a direct result of the lesions, largely due to brain hemorrhages.

Seizures and headaches are the most generalized symptoms of AVMs, but no particular type of seizure or headache pattern has been identified. Seizures can be partial or total, involving a loss of control over movement, convulsions, or a change in a person's level of consciousness. Headaches can vary greatly in frequency, duration, and intensity, sometimes becoming as severe as migraines. Sometimes a headache consistently affecting one side of the head may be closely linked to the site of an AVM. More frequently, however, the location of the pain is not specific to the lesion and may encompass most of the head.

AVMs also can cause a wide range of more specific neurological symptoms that vary from person to person, depending primarily upon the location of the AVM. Such symptoms may include muscle weakness or paralysis in one part of the body; a loss of coordination (ataxia) that can lead to such problems as gait disturbances; apraxia, or difficulties carrying out tasks that require planning; dizziness; visual disturbances such as a loss of part of the visual field; an inability to control eye movement; papilledema (swelling of a part of the optic nerve known as the optic disk); various problems using or understanding language (aphasia); abnormal sensations such as numbness, tingling, or spontaneous pain (paresthesia or dysesthesia); memory deficits; and mental confusion, hallucinations, or dementia. Researchers have recently uncovered evidence that AVMs may also cause subtle learning or behavioral disorders in some people during their childhood or adolescence, long before more obvious symptoms become evident.

One of the more distinctive signs indicating the presence of an AVM is an auditory phenomenon, or bruit: the rhythmic, whooshing sound caused by excessively rapid blood flow through the arteries and veins of an AVM. When audible to patients, bruit may compromise hearing, disturb sleep, or cause significant psychological distress.

Symptoms caused by AVMs can appear at any age, but because these abnormalities tend to result from a slow buildup of neurological damage over time they are most often noticed when people are in their twenties, thirties, or forties. If AVMs do not become symptomatic by the time people reach their late forties or early fifties, the lesions tend to remain stable and rarely produce symptoms. In women, pregnancy sometimes causes a sudden onset or worsening of symptoms, due to accompanying cardiovascular changes, especially increases in blood volume and blood pressure.

In contrast to the vast majority of neurological AVMs, one especially severe type causes symptoms to appear at, or very soon after, birth. Called a vein of Galen defect after the major blood vessel involved, this lesion is located deep inside the brain. It is frequently associated with hydrocephalus (swelling of the brain, often with visible enlargement of the head), swollen veins visible on the scalp, seizures, failure to thrive, and congestive heart failure. Children born with this condition who survive past infancy often remain developmentally impaired.

AVMs become symptomatic only when the damage they cause to the brain or spinal cord reaches a critical level. This is one of the reasons why a relatively small fraction of people with these lesions experiences significant health problems related to the condition. AVMs damage the brain or spinal cord through three basic mechanisms: by reducing the amount of oxygen reaching neurological tissues; by causing bleeding (hemorrhage) into surrounding tissues; and by compressing or displacing parts of the brain or spinal cord.

AVMs compromise oxygen delivery to the brain or spinal cord by altering normal patterns of blood flow. Arteries and veins are normally interconnected by a series of progressively smaller blood vessels that control and slow the rate of blood flow. Oxygen delivery to surrounding tissues takes place through the thin, porous walls of the smallest of these interconnecting vessels, known as capillaries, where the blood flows most slowly. The arteries and veins that make up AVMs, however, lack this intervening capillary network. Instead, arteries dump blood directly into veins through a passageway called a fistula. The flow rate is uncontrolled and extremely rapid, too rapid to allow oxygen to be dispersed to surrounding tissues. When starved of normal amounts of oxygen, the cells that make up these tissues begin to deteriorate, sometimes dying off completely.

This abnormally rapid rate of blood flow frequently causes blood pressure inside the vessels located in the central portion of an AVM directly adjacent to the fistula, the nidus, to rise to dangerously high levels. The arteries feeding blood into the lesion often become swollen and distorted; the veins that drain blood away from it often become abnormally constricted (a condition called stenosis). Moreover, the walls of the involved arteries and veins are often abnormally thin and weak. Aneurysms (balloon-like bulges in blood vessel walls that are susceptible to rupture) may develop in association with approximately half of all neurological AVMs due to this structural weakness.

Bleeding can result from this combination of high internal pressure and vessel wall weakness. Such hemorrhages are often microscopic in size, causing limited damage and few significant symptoms. Even many nonsymptomatic AVMs show evidence of past bleeding. But massive hemorrhages can occur if the physical stresses caused by extremely high blood pressure, rapid blood flow rates, and vessel wall weakness are great enough. If a large enough volume of blood escapes from a ruptured AVM into the surrounding brain, the result can be a catastrophic stroke. AVMs account for approximately two percent of all hemorrhagic strokes that occur each year.

Even in the absence of bleeding or significant oxygen depletion, large AVMs can damage the brain or spinal cord simply by their presence. They can range in size from a fraction of an inch to more than 2.5 inches in diameter, depending on the number and size of the blood vessels making up the lesion. The larger the lesion, the greater the amount of pressure it exerts on surrounding brain or spinal cord structures. The largest lesions may compress several inches of the spinal cord or distort the shape of an entire hemisphere of the brain. Such massive AVMs can constrict the flow of cerebrospinal fluid by distorting or closing the passageways and open chambers, or ventricles, inside the brain that allow this fluid to circulate freely. As cerebrospinal fluid accumulates, neurological tissues begin to swell, and in extreme cases, hydrocephalus results. This fluid buildup further increases the amount of pressure on fragile neurological structures, adding to the damage caused by the AVM itself.

AVMs can form virtually anywhere in the brain or spinal cord, wherever arteries and veins exist. Some are formed from blood vessels located in the dura mater or in the pia mater, the outermost and innermost, respectively, of the three membranes surrounding the brain and spinal cord. (The third membrane, called the arachnoid, lacks blood vessels.)

AVMs affecting the spinal cord are of two types, AVMs of the dura mater, which affect the function of the spinal cord by transmitting excess pressure to the venous system of the spinal cord; and AVMs of the spinal cord itself, which affect the function of the spinal cord by hemorrhage by reducing blood flow to the spinal cord, or by causing excess venous pressure. Spinal AVMs frequently cause attacks of sudden, severe back pain, often concentrated at the roots of nerve fibers where they exit the vertebrae; the pain is similar to that caused by a slipped disk. These lesions also can cause sensory disturbances, muscle weakness, or paralysis in the parts of the body served by the spinal cord or the damaged nerve fibers. Spinal cord injury by the AVM by either of the mechanisms described above can lead to degeneration of the nerve fibers within the spinal cord below the level of the lesion, causing widespread paralysis in parts of the body controlled by those nerve fibers.

Dural and pial AVMs can appear anywhere on the surface of the brain. Those located on the surface of the cerebral hemispheres exert pressure on the cerebral cortex. Depending on their location, these AVMs may damage portions of the cerebral cortex involved with thinking, speaking, understanding language, hearing, taste, touch, or initiating and controlling voluntary movements. AVMs located on the frontal lobe close to the optic nerve or on the occipital lobe, the rear portion of the cerebrum where images are processed, may cause a variety of visual disturbances.

AVMs also can form from blood vessels located deep inside the interior of the cerebrum. These AVMs may compromise the functions of three vital structures: the thalamus, which transmits nerve signals between the spinal cord and upper regions of the brain; the basal ganglia surrounding the thalamus, which coordinate complex movements; and the hippocampus, which plays a major role in memory.

AVMs can affect other parts of the brain besides the cerebrum. The hindbrain is formed from two major structures: the cerebellum, which is nestled under the rear portion of the cerebrum, and the brainstem, which serves as the bridge linking the upper portions of the brain with the spinal cord. These structures control finely coordinated movements, maintain balance, and regulate some functions of internal organs, including those of the heart and lungs. AVM damage to these parts of the hindbrain can result in dizziness, giddiness, vomiting, a loss of the ability to coordinate complex movements such as walking, uncontrollable muscle tremors, or disruptions in organ function (for example, heart failure).

The greatest potential danger posed by AVMs is hemorrhage. Researchers believe that each year between two and four percent of all AVMs hemorrhage. Most episodes of bleeding remain undetected at the time they occur because they are not severe enough to cause significant neurological damage. But massive, even fatal, bleeding episodes do occur. The present state of knowledge does not permit doctors to predict whether or not any particular person with an AVM will suffer an extensive hemorrhage. The lesions can remain stable or can suddenly begin to grow. In a few cases, they have been observed to regress spontaneously.

Besides AVMs, three other main types of vascular lesion can arise in the brain or spinal cord: cavernous malformations, capillary telangiectases, and venous malformations. These lesions may form virtually anywhere within the central nervous system, but unlike AVMs, they are not caused by high-velocity blood flow from arteries into veins. In contrast, cavernous malformations, telangiectases, and venous malformations are all low-flow lesions. Instead of a combination of arteries and veins, each one involves only one type of blood vessel. These lesions are less unstable than AVMs and do not pose the same relatively high risk of significant hemorrhage. In general, low-flow lesions tend to cause fewer troubling neurological symptoms and require less aggressive treatment than do AVMs.

Cavernous malformations are lesions formed from groups of tightly packed, abnormally thin-walled, small blood vessels that displace normal neurological tissue in the brain or spinal cord. The vessels are filled with slow-moving or stagnant blood that is usually clotted or in a state of decomposition. Like AVMs, cavernous malformations can range in size from a few fractions of an inch to several inches in diameter, depending on the number of blood vessels involved. Some people develop multiple lesions. Although cavernous malformations usually do not hemorrhage as severely as AVMs do, they sometimes leak blood into surrounding neurological tissues because the walls of the involved blood vessels are extremely fragile. Although they are often not as symptomatic as AVMs, cavernous malformations can cause seizures in some people. After AVMs, cavernous malformations are the type of vascular lesion most likely to require treatment.

Capillary telangiectases are lesions that consist of groups of abnormally swollen capillaries and usually measure less than an inch in diameter. Capillaries are the smallest of all blood vessels, with diameters smaller than that of a human hair; they have the capacity to transport only small quantities of blood, and blood flows through these vessels very slowly. Because of these factors, telangiectases rarely cause extensive damage to surrounding brain or spinal cord tissues. Any isolated hemorrhages that occur are microscopic in size.

Thus, the lesions are usually benign. However, in some inherited disorders in which people develop large numbers of these lesions, telangiectases can contribute to the development of nonspecific neurological symptoms such as headaches or seizures.

Finally, venous malformations are lesions that consist of abnormally enlarged veins. The structural defect usually does not interfere with the function of the blood vessels, which is to drain oxygen-depleted blood away from the body's tissues and return it to the lungs and heart. Venous malformations rarely hemorrhage. As with telangiectases, most venous malformations do not produce symptoms, remain undetected, and follow a benign course.

Physicians now use an array of traditional and new imaging technologies to uncover the presence of AVMs. Angiography provides the most accurate pictures of blood vessel structure in AVMs. The technique requires injecting a special water-soluble dye, called a contrast agent, into an artery. The dye highlights the structure of blood vessels so that it can be recorded on conventional X-rays. Although angiography can record fine details of vascular lesions, the procedure is somewhat invasive and carries a slight risk of causing a stroke.

Two of the most frequently employed noninvasive imaging technologies used to detect AVMs are computed axial tomography (CT) and magnetic resonance imaging (MRI) scans. CT scans use X-rays to create a series of cross-sectional images of the head, brain, or spinal cord and are especially useful in revealing the presence of hemorrhage. MRI imaging, however, offers superior diagnostic information by using magnetic fields to detect subtle changes in neurological tissues. A recently developed application of MRI technology (magnetic resonance angiography or MRA) can record the pattern and velocity of blood flow through vascular lesions as well as the flow of cerebrospinal fluid throughout the brain and spinal cord. Both MRI and MRA can provide three-dimensional representations of AVMs by taking images from multiple angles.

Medication can often alleviate general symptoms such as headache, back pain, and seizures caused by AVMs and other vascular lesions. However, the definitive conventional treatment for AVMs is surgery.

The decision to perform surgery on any individual with an AVM requires a careful consideration of possible benefits versus risks. The natural history of an individual AVM is difficult to predict; however, left untreated, they have the potential of causing significant hemorrhage, which may result in serious neurological deficits or death. On the other hand, surgery on any part of the central nervous system carries its own risks as well; AVM surgery is associated with an estimated eight percent risk of serious complications or death. There is no easy formula that can allow physicians and their patients to reach a decision on the best course of therapyCCall therapeutic decisions must be made on a case-by-case basis.

Today, three surgical options exist for the treatment of AVMs: conventional surgery, radiosurgery, and endovascular embolization.

Conventional surgery involves entering the brain or spinal cord and removing the central portion of the AVM, including the fistula, while causing as little damage as possible to surrounding neurological structures. One description of this type of surgical treatment is described in Hillman and Pare, the disclosures of which are incorporated herein by reference. (Hillman, J.; "Population based analysis of arteriovenous malformation treatment" J. Neurosurg., 2001 October; 95(4): 633 637; and Pare, M. C., Bojanowski, M., "Surgical Treatment of AVMs in Eloquent Zones of the Brain: Apropos of Eleven Cases", Ann. Chir., 1991; 45(9): 811 5.) This surgery is most appropriate when an AVM is located in a superficial portion of the brain or spinal cord and is relatively small in size. However, AVMs located deep inside the brain generally cannot be approached through conventional surgical techniques because there is too great a possibility that functionally important brain tissue will be damaged or destroyed.

Endovascular embolization and radiosurgery are less invasive than conventional surgery and offer safer treatment options for AVMs located deep inside the brain. Radiosurgery is the least invasive therapeutic approach. It involves aiming a beam of highly focused radiation directly on the AVM. The high dose of radiation damages the walls of the blood vessels making up the lesion. Radiosurgical techniques have been described by Wallace and Irie, the disclosures of which are incorporated herein by reference. (Wallace, R., Bourekas, E., "Brain Arteriovenous Malformations", Neuroimaging Clin. N. America, 1998 May; 8(2): 383 99; and Irie, K., Nagao, S., Honma, Y., Kunishio, K., Ogawa, T., Kawai, N. "Treatment of arteriovenous malformation of the brain preliminary experience", J. Clin. Neurosci., 2000 September; 7 Supple 1:24 29.) Over the course of the next several months, the irradiated vessels gradually degenerate and eventually close, leading to the resolution of the AVM.

Although radiosurgery is minimally invasive, it is not as effective as conventional surgery. Radiosurgery often has incomplete results, particularly when an AVM is large, and it poses the additional risk of radiation damage to surrounding normal tissues. Moreover, even when successful, complete obliteration of an AVM takes place over the course of many months following radiosurgery. During that period, the risk of hemorrhage is still present, and may in fact be higher.

The most promising technique is endovascular embolization. In this technique the surgeon guides a catheter though the arterial network until the tip reaches the site of the AVM. The surgeon then introduces a substance that will plug the malformation, correcting the abnormal pattern of blood flow. This process is known as embolization because it causes an embolus (a material which can obstruct or occlude blood flow) to travel through blood vessels, eventually becoming lodged in a vessel and obstructing blood flow. Embolization techniques are discussed generally by Jizong, Liu, Vernon, and Wallace the disclosures of which are incorporated herein by reference. (Jizong, Z., Shou, W., Jingsheng, L., Dali, S., Yuanli, Z., Yan, Z., "Combination of intraoperative embolisation with surgical resection for treatment of giant cerebral arteriovenous malformations", J. Clin. Neurosci., 2000 September; 7 Suppl. 1:54 59; Liu, H. M., Huang, Y. C., Wang, Y. H., "Embolization of cerebral arteriovenous malformations with n butyl 2 cyanoacrylate", J. Formos. Med. Addoc., 2000 December; 99(12):906 913; Vernon, B., et al., "Water Borne, in situ Cross Linked Biomaterials from Phase Segregated Precursors", Submitted Article to Journal of Biomedical Materials *Research. February* 2002; and Wallace, R., et al., "The Safety and Effectiveness of Brain AVM Embolization using Acrylic and Particles: The Experience of a Single Institution", Neurosurgery, 1995 October; 37(4); 606 18.)

The materials used to create an obstruction, occlusion or embolus in the center of an AVM include fast-drying biologically inert glues, fibered titanium coils, and tiny balloons. However, conventional embolization frequently proves incomplete or temporary because the materials being used degrade over time. Since embolization usually does not permanently obliterate the AVM, it is usually used only as an adjunct to surgery to reduce the blood flow through the AVM and make the surgery safer. Moreover, conventional AVM embolization materials (e.g. cyanoacrylates), stick to vessels. For example, cyanoacrylates used in known embolization materials have been known to glue catheters to vessels. These materials are also known to cause vessel cell wall damage or stress in AVM vasculature increasing the chance of incomplete occlusion, vessel rupture or hemorrhage.

To avoid this adhesion, other systems have also been investigated. Preformed polymers dissolved in water miscible organic solvents, such as Dimethyl Sulfoxide (DMSO), have been used for this application clinically. With these materials the polymer precipitates after injection into the vasculature as the solvent is replaced by water. Improvements have been made by replacing the DMSO with less toxic solvents such as N-methyl pyrrolidone (NMP). A further improvement would be the complete elimination of organic solvents with aqueous systems.

Recently, the advantages of waterborne, self-reactive systems have been recognized for this application. In fact two in situ gelling systems have been investigated recently. These are calcium alginate and thermally responsive polymers based on N-isopropylacrylamide. The calcium alginate systems developed by Becker et. al., the disclosure of which is incorporated herein by reference, proved to be biocompatible and mechanically stable; however, this procedure requires the simultaneous injection of two components delivered from two catheters position in separate locations in the vasculature: proximal and distal to the AVM or by double lumen catheters, restricting the viscosity (and thus gel strength) that can be delivered or increasing the catheter diameter and reducing the vessel accessibility. (Becker, T. et al., "Calcium Algenate Gel: A biocompatible and mechanically stable polymer for endovascular treatment", Journal of Biomedical Materials Research., Vol. 54 (2001), pp. 76 86.)

Accordingly, a need exists for improved embolization materials that would allow safer and more permanent minimally invasive relief of AVMs.

SUMMARY OF THE INVENTION

The present invention is directed to an improved in situ gelling materials for use in embolization medical treatments.

In one embodiment, the AVM occluding gelling material of the current invention consists of a combination of a nucleophilic component and a component containing a conjugated unsaturated bond.

In another embodiment, the gelling material comprises thiole precursors, acrylate precursors and a PBS buffer.

In still another embodiment, the gelation period of the hydrogel of the current invention may be controlled through the composition of the buffer.

In yet another embodiment, the hydrogel of the current invention may include a radio-opaque contrast agent so that the hydrogel can be imaged using fluoroscopy as the gel is being injected through the catheter and into the AVM.

In still yet another embodiment, the hydrogel of the current invention can be introduced to the AVM through a single lumen catheter.

In still yet another embodiment, the current invention is directed to methods of using the AVM occluding hydrogels for use in occluding or blocking arteriovenous malformations, or abnormal vasculature in the brain.

In still yet another embodiment, the current invention is directed to methods of using the AVM occluding hydrogels for occluding aneurisms and blocking fistulas, or vessels of any type.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
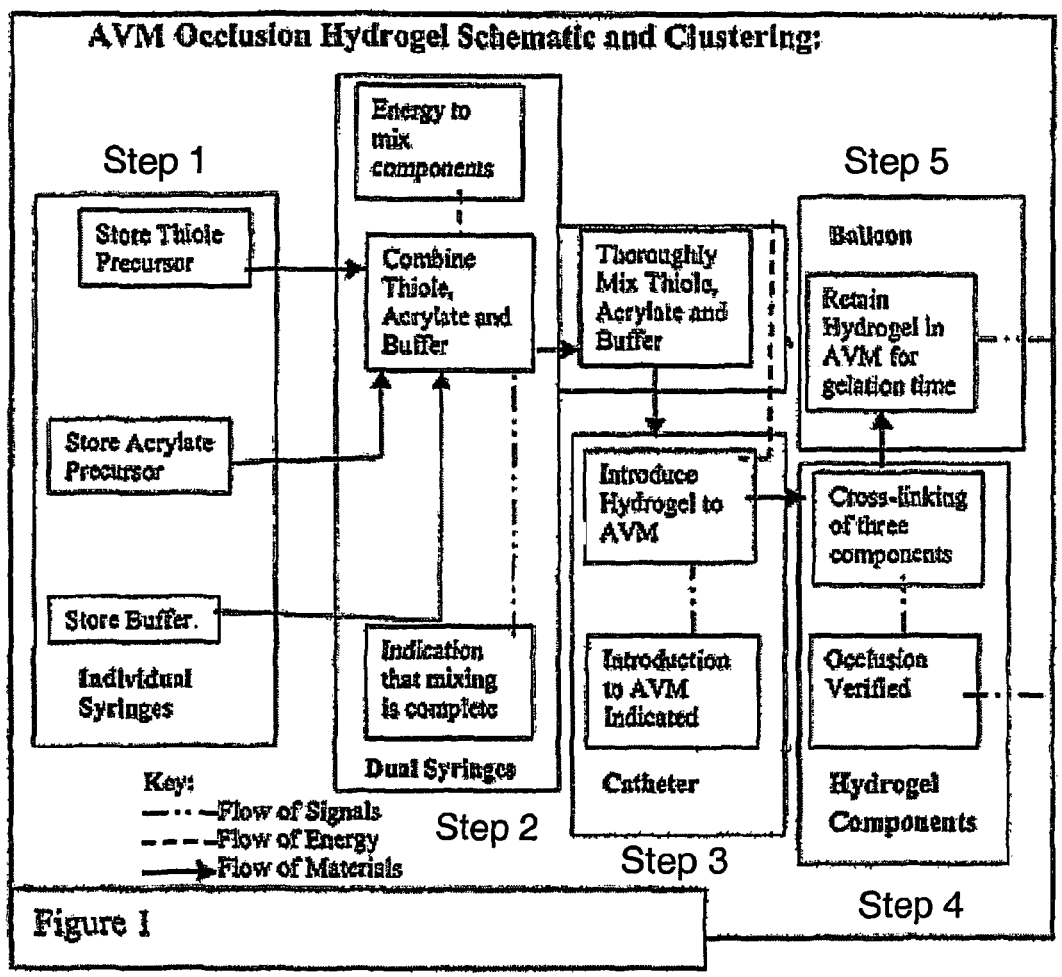
FIG. 1, shows a flowchart of an exemplary method of using an in situ occluding gelling material in accordance with the current invention.

The present invention is directed to a novel in situ occluding gelling material for use in occluding or blocking arteriovenous malformations (AVMs), or abnormal vasculature in the body during an embolization procedure. The invention is based on a chemical reaction in which two or more precursor components, namely a nucleophilic component and a component containing a conjugated unsaturated bond, are polyermized or crosslinked in situ in a self-selective manner. The invention depends on the observation that these precursor components are self-selective in their reaction rates. In other words, the nucleophilic component reacts faster with the component containing a conjugated unsaturated bond than with other components present during the reaction, and the component containing a conjugated unsaturated bond reacts faster with the nucleophilic compound than with other components present during the reaction.

The functionalities of the precursor components will affect the resulting polymerization product. The word "functionality" as used herein refers to the number of reactive sites, as generally used in polymer science. Mixing two components each having a functionality of two results in a linear polymeric biomaterial. If one of the components has a functionality of more than two, mixing of the components will result in a cross-linked polymeric biomaterial. In cross-linked biomaterials, the components can be very hydrophilic, and the overall material can yet remain as an intact solid, not dispersing throughout the body. If such a non-dispersing system is desired for a linear polymeric biomaterial, it is useful if at least one precursor component be hydrophobic, such that the resulting biomaterial also be insoluble in water or body fluids.

The present invention makes use of a Michael-type addition reaction between the nucleophilic component and the component containing a conjugated unsaturated bond. The reaction can be exemplified as follows:

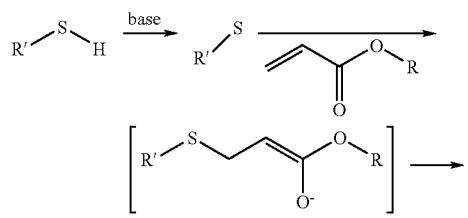

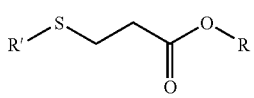

Such Michael-type addition reactions can be performed on a wide variety of conjugated unsaturated compounds in accordance with the invention. Exemplary conjugated unsaturated compounds include those having structures 1 to 20 set forth below.

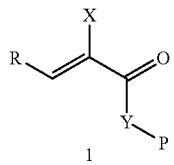

X = H, CH₃, CN, COOW
R = H, W, Ph
Y = NH, O, 1,4-Ph
W = C1-C5 linear aliphatic chain

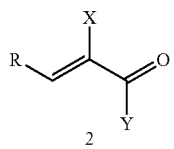

X = CN, COOW
Y = OW, Ph
W = C1-C5 linear aliphatic chain

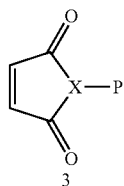

X = N, CH

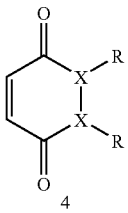

A  X = CH; Y = CH; R = H, W—P; W = NH, O, nihil
B  X = N; Y = N; R = H, P
C  X—Y = C≡C; R = W—P; W = NH, O, nihil

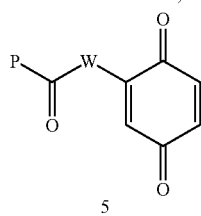

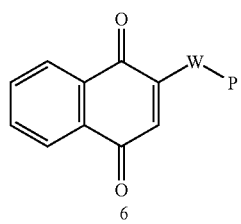

-continued

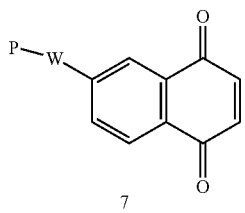

7

W = NH, O, nihil

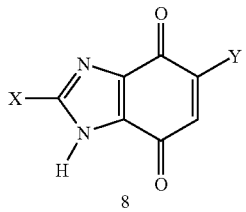

8

X, Y = (H, P), (P, P), (P, H), (P, aliphatic chain)

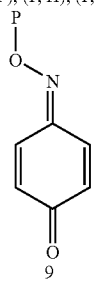

9

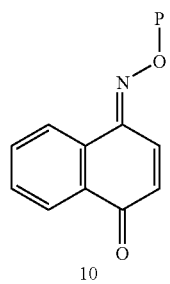

10

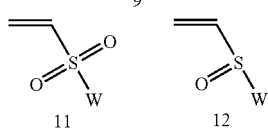 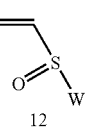 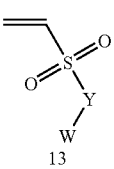 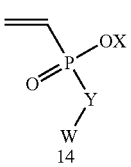

11    12    13    14

W = P, 1,4-Ph—P
Y = O, NH
X = P, alkali or alkali earth metal ion

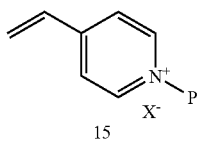

15

X = halogen, sulphonate

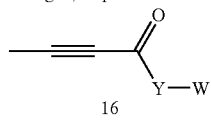 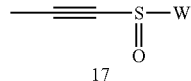 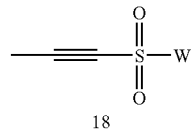

16    17    18

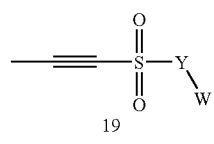 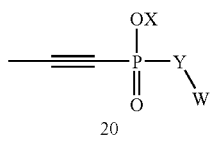

19    20

Y = O, NH
X = P, alkali or alkali earthmetal ion
W = P, 1,4-Ph—P

In these structures, P indicates an oligomeric or polymeric structure, examples of which are discussed further below. In structures 1 to 20, P is intended as terminated with a CH$_2$, CH or C group. Reactive double bonds can be conjugated to one or more carbonyl groups in a linear ketone, ester or amide structure (1, 2) or to two in a ring system, as in a maleic or paraquinoid derivative (3, 4, 5, 6, 7, 8, 9, 10). In the latter case, the ring can be fused to give a naphthoquinone (6, 7, 10) or a 4,7-benzimidazoledione (8), and the carbonyl groups can be converted to an oxime (9, 10). The double bond can be conjugated to a heteroatom-heteroatom double bond, such as a sulfone (11), a sulfoxide (12), a sulfonate or a sulfonamide (13), or a phosphonate or phosphonamide (14). Alternatively, the double bond can be conjugated to an electron-poor aromatic system, such as a 4-vinylpirydinium ion (15). Triple bonds can be used in conjugation with carbonyl or heteroatom-based multiple bonds (16, 17, 18, 19, 20).

Specifically, structures such as 1 and 2 are based on the conjugation of a carbon-carbon double bond with one or two electron-withdrawing groups. One of them is always a carbonyl, increasing the reactivity passing from an amide, to an ester, and then to a phenone structure. The nucleophilic addition is easier upon decreasing the steric hindrance, or increasing the electron-withdrawing power in the alpha-position: $CH_3<H<COOW<CN$.

The higher reactivity obtained by using the last two structures can be modulated by varying the bulkiness of the substituents in the beta-position. where the nucleophilic attack takes place. The reactivity decreases in the order $P<W<Ph<H$. So the position of P too can be used to tune the reactivity towards nucleophiles. This family includes some 10 compounds for which a great deal is known about their toxicology and use in medicine. For example, water-soluble polymers with acrylates and methacrylates on their termini are polymerized (by free radical mechanisms) in vivo, in hydrogel sealants and bone cements, respectively. Thus, acrylate and methacrylate-containing polymers have been seen in the body before in clinical products, but for use with a dramatically different chemical reaction scheme.

The structures 3 to 10 exhibit very high reactivity towards nucleophiles, due both to the cis configuration of the double bond and the presence of two electron-withdrawing groups. Unsaturated ketones react faster than amides or imides, due to the stronger electronegativity of these carbonyl groups. So, cyclopentendione derivatives react faster than maleimidic ones (3), and para-quinones react faster than maleic hydrazides (4) and also faster than cyclohexanones, due to more extended conjugation. The highest reactivity is shown by naphthoquinones (7).

P can be placed in positions where it does not reduce the reactivity of the unsaturated group, that is in the opposite part of the ring (3, 5), on another ring (7, 8) or O-linked through a para-quinone mono-oxime (9, 10). P can be also linked to the reactive double bond (6, 8), particularly if the nucleophilic addition rate is to be decreased.

The activation of double bonds to nucleophilic addition can be obtained also by using heteroatom-based electron-withdrawing groups. In fact, heteroatom-containing analogs of ketones (11, 12), esters and amides (13, 14) provide a similar electronic behavior. Structures 13 and 14 can also be used as easily hydrolyzable groups that can promote a quick gel degradation. The reactivity towards nucleophilic addition increases with electronegativity of the group, that is in the order $11>12>13>14$, and is enhanced by the linkage with an aromatic ring. A strong activation of double bonds can also be obtained, using electron-withdrawing groups based on aromatic rings. Any aromatic structure containing a pyridinium-like cation (e.g., derivatives of quinoline, imidazole, pyrazine, pyrimidine, pyridazine, and similar sp containing compounds) strongly polarizes the double bond and makes possible quick Michael-type additions.

Carbon-carbon triple bonds, conjugated with carbon- or heteroatom-based electron-withdrawing groups, can easily react with sulphur nucleophiles, to give products from simple and double addition. The reactivity is influenced by the substituents, as for the double bond-containing analogous compounds.

Particularly preferred conjugated unsaturated compounds for use in the invention include acrylates, vinylsulfones, acrylamides, quinones and vinylpyridiniums, with acrylates being particularly preferred.

The nucleophiles that are useful are those that are reactive towards conjugated unsaturated groups by way of Michael-type addition reactions. The reactivity of the nucleophile depends on the identity of the unsaturated group, but the identity of the unsaturated group is first limited by its reaction with water at physiologic pH. Thus, useful nucleophiles will generally be more nucleophilic than water at physiologic pH. Preferred nucleophiles are those that are commonly found in biological systems. for reasons of toxicology, but ones that are not commonly found free in biological systems outside of cells. Thus, while there may be examples in which amines can be employed as effective nucleophiles, the most preferred nucleophile is the thiol.

Thiols are present in biological systems outside of cells in paired form, as disulfide linkages. When the highest degree of self-selectivity is desired (e.g., when a therapeutic protein is incorporated, when the gelation reaction is conducted in the presence of tissue and chemical modification of that tissue is not desirable), then a thiol will represent the strong nucleophile of choice.

There are other situations, however, when the highest level of self-selectivity may not be necessary. This would include situations when no therapeutic protein is incorporated and when the gelation reaction is conducted in situ, but when chemical bonding to the tissue is either desirable or is not undesirable. In these cases, an amine may serve as an adequate nucleophile. Here, particular attention is paid to the pH, in that the deprotonated amine is a much stronger nucleophile than the protonated amine. Thus, for example, the alpha amine on a typical amino acid (pK as low as 8.8 for asparagine, average of 9.0 for all 20 common amino acids except proline) has a much lower pK than the side chain epsilon amine of lysine (pK 10.80). As such, if particular attention is paid to the pK of an amine used as the strong nucleophile, substantial self-selectivity can be obtained. Proteins have only one alpha amine (on the N-terminus). By selection of an amine with a low pK, and then formulation of the final precursor solution such that the pH were near that pK, one could favor reaction of the unsaturation provided with the amine provided, rather than other amines present in the system. In cases where no self selectivity is desired, one need pay less attention to the pK of the amine used as the nucleophile. However to obtain reaction rates that are acceptably fast one must adjust the pH of the final precursor solution such that an adequate number of these amines are deprotonated.

The term "nucleophilic group" as used herein includes not only the functional groups themselves (e.g., thiol or amine), but also molecules that contain the functional group (e.g., cysteine or cystyl residue, or lysine or lysyl residue). The nucleophilic groups may be contained in molecules with great flexibility in overall structure. For example, a difunctional nucleophile could be presented in the form of Nuc-P-Nuc, where P has the meaning discussed above, and Nuc refers to the nucleophile. Likewise, a branched polymer P could be derivatized with a number of nucleophiles to create $P\text{-}(Nuc)_i$, where i=2 would be useful. Nuc needs not be displayed at the chain termini of P. For example, a repeating structure could be envisioned: $(P\ Nuc)_i$ where i=2 would be useful. Clearly, not all of the P or Nuc groups in such a structure need to be identical. It is only necessary that one nucleophilic precursor contain greater than or equal to two such Nuc groups.

Likewise, similar structures of P and the conjugated unsaturated groups described above may be formed. It is only necessary that one conjugated unsaturated precursor contain greater than or equal to two such conjugated unsaturated groups.

It should be noted and understood, that it is not necessary that both precursor components, for example, both the nucleophilic precursor component and the conjugated unsaturated precursor component, actually be polymeric in the usual sense of the word. It is only the functionality that matters. In practice, it is convenient if at least one component is polymeric in the usual sense of the word, but this is not absolutely necessary. For example, useful. materials result from the reaction of a PEG triacrylate with dicysteine, and likewise, useful materials result from the reaction of a PEG trithiol and a low molecular weight diacrylate. Further, useful materials for some applications also result from reaction of a dicysteine and a low molecular diacrylate.

In practice, it is convenient and useful when one or more precursor component is polymeric in the usual sense of the word. In these cases, P can be a synthetic hydrophilic polymer, a synthetic hydrophobic polymeric liquid, a synthetic hydrophobic polymer that is soluble in solvents of acceptable toxicity or biological influence for the envisioned application, a biosynthetic protein or peptide, a naturally occurring protein or processed naturally occurring protein, or a polysaccharide.

As noted above, thiols are of particular interest as the nucleophilic component. Although proteins contain the amino acid cysteine, the side chain of which terminates in a thiol, there are very few free thiols within proteins. Most proteins contain an even number of cysteine residues, and these are then paired and form disulfide cross-links between various regions of the protein. Some proteins contain an odd number of cysteine residues, and most of these are present as disulfide linked dimers, again resulting in no free thiol residues being present in the native protein. Thus, there are very few free thiols in proteins. Some important electron transferring molecules, such as glutathione, contain a free thiol, but these molecules are generally restricted in their spatial location to the inside of a cell. Conjugated unsaturated structures presented outside the cell will be substantially unreactive with most proteins at near-physiological conditions. Accordingly, using a thiol with the component containing a conjugated unsaturated bond in the mixture of the invention will react in a very self-selective manner.

Turning now to the P group, P can be a polymer such as poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly (vinyl pyrrolidone), poly(ethylene-co-vinyl pyrrolidone), poly(maleic acid), poly(ethylene-co-maleic acid), poly(acrylamide), or a poly(ethylene oxide)-co-poly(propylene oxide) block copolymers. This is not an exhaustive list, as other hydrophilic polymers could also be used. P can also be a copolymer, a block copolymer, a graft copolymer, or a random copolymer. Blocks, which are polymerized on the ends of the hydrophilic polymers, can be composed of, for example, lactic acid, glycolic acid, epsilon-caprolactone, lactic-co-glycolic acid oligomers, trimethylene carbonate, anhydrides, and/or amino acids, for example, to confer degradability by hydrolytic or enzymatic means.

P can also be selected to create a hydrophobic system, for example, by using a water-dispersible liquid such as polypropylene glycol. Even if P is not a hydrophobic polymer, the component containing P can be made hydrophobic, such as with pentaerythritol-tetrakis (3-mercaptopropionate) and pentaerythritol triacrylate (where the P group is pentaerythritol).

Random copolymers can be based on vinyl alcohol, such as poly(N vinylpyrroliclone-co-vinyl alcohol) or poly(ethylene-co-vinvl alcohol), with different compositions, can be derivatized with conjugated unsaturated groups, such as acrylates, benzoquinones, naphthoquinones and others. The vinyl alcohol copolymers can be functionalized with $(CH_2)_n COOH$ groups by reaction with ω-bromo-carboxylic acids. The resulting polymers or acrylic or methacrylic acid copolymers can be used for the attachment of quinone groups. Comonomer composition and extent of functionalization do not dramatically influence the reaction rates, unless they determine solubility or phase transition. On the other hand, they determine the final mechanical properties.

Alternatively, P may be a protein or peptide. Examples of suitable proteins and peptides for use in the invention are disclosed in International Patent Publication No. WO 00/44808, the entire disclosure of which is incorporated herein by reference.

Utilizing terminology from polymer science, polymers can be made by reaction of monomers with a functionality of 2. Cross-linked networks of polymers can be made if some or all of the monomers have a functionality greater than 2. Molecules are described herein having a functionality greater than or equal to 2 (monomers or macromers), which can be reacted together to form a cross-linked network, where functionality is defined in terms of addition reactions. As used herein, polymerization refers to the reaction of monomers or macromers with functionality of 2, and cross-linking refers to the reaction of monomers or macromers some or all of which have a functionality greater than 2. The term monomers here is not limited to small molecules, but can also refer to polymers and biopolymers.

The monomers described are of two classes, which when reacted together form a linear or cross-linked biomaterial. Both classes of monomers are required to be mixed together for cross-linking to occur. One class of monomer contains 2 or more conjugated unsaturated groups (thus, a functionality of 2 or more), preferably conjugated. The other class of monomer contains 2 or more nucleophiles (thus, a functionality of 2 or more), preferably nucleophiles that are stronger nucleophiles than others present as other components of the system.

When water-soluble or water-dispersible precursor monomers are mixed together (referred to as the final precursor solution), linear or cross-linked gels or networks are formed, and such reactions can proceed in water at physiologic or nearly-physiologic salt concentrations and pH. It is not necessary that the monomers be entirely soluble in water, and indeed it is sometimes beneficial that they not be soluble in water. In such cases, gels may not be obtained as the final material, but rather more hydrophobic, less water-swelling materials. These can be particularly useful in the delivery of hydrophobic drugs and in the formation of materials with substantial structural strength. It is only necessary that the two components be either soluble in each other or at least finely dispersible in each other, perhaps in the presence of an emulsifying agent. In this manner, the two components can come close enough to each other to react to form the linear or cross-linked material.

It is also possible to work with solutions of monomers formed in a solution other than water. For example, the use of N-methyl pyrrolidone (NMP) as a solvent in injectable biomaterial systems is known, and as such it is possible, when one wishes to work with the precursor components in solution, but with precursor components that are not freely soluble in water, to employ certain organic solvents that are acceptable for use with the sensitive biological material under consideration.

When the biomaterial is being formed in the body, as in the present invention, the list of acceptable solvents is dominated by toxicity concerns. For this application, NMP is a particularly favorable organic solvent. The toxicity of the solvent system can also be modulated by employing a mixed solvent system, comprising the organic solvent and water, to lower the overall concentration of organic solvent but to still provide good solubility or dispersability in the mixed solvent system.

Other considerations are important for the reaction occurring in situ. For example, the reactants are desirably stable in water when the precursor solutions are prepared in water. Stable is defined as reacting slowly, with slowly defined as sufficiently slow to allow the reaction between the two components to proceed and still result in the formation of the desired biomaterial. Additionally, the addition reaction in the final precursor solution is preferably not exothermic to the point of causing tissue damage, drug breakdown or other detrimental results to the biological material under consideration. The temperature of the gelling solution generally should not be raised above 60° C. during gelation, and preferably even cooler maximum reaction temperatures are desirable. Further, the components of the precursor solution must not be toxic at concentrations that diffuse out of the final precursor solution as it is applied, with the word toxic being defined as inducing a medically unacceptable tissue reaction in a medically relevant context.

In a preferred embodiment, the invention employs a thiol as the nucleophilic component and an acrylate as the component containing a conjugated unsaturated bond. Particularly preferred thiols include pentaerythritol-tetrakis(3-mercaptopropionate) (QT) and poly(ethylene glycol)hexathiol (PEGHT). Particularly preferred acrylates include poly(ethyleneglycol) diacrylate 570 (PEGDA), poly(propylene glycol)diacrylate 900 (PPODA), pentaerythritol triacrylate (TA), and poly(ethylene glycol)tetraacrylate (QA). Acrylates react orders of magnitude faster with thiols than with amines and other mucleophiles present in biological samples, where free thiols are present in negligible leachable content. Such a system is also waterborned and, before gelations, possesses low viscosity, allowing delivery through a microcatheter. The Michael-type addition reaction, being pH-activated, allows, for certain combinations of reagents, premixing of the reagents without reaction, while the reaction can be started at a desired time by addition of a base. The above-noted monomeric multifunctional materials are dispersed in water at high solid content, typically 75 wt %.

As discussed in the summary, these materials can be made radiopaque by including in the reaction mixture a suitable radiopaque agent, such as barium sulfate, tantalum, iohexol (commercially available under the name Omnipaque from Amersham Health, Princeton, N.J.), iothalamate meglumine (commercially available under the name Contray from Mallinckckrodt, St. Louis, Mo.), ioxaglate meglumine and ioxaglate sodium (commercially available as a mixture under the name Hexabrix from Mallinckrodt, St. Louis, Mo.).

The liquid mixture preferably also comprises a buffer, such as phosphate buffered saline (PBS). Other components can also be included within the liquid mixture, such as a base for adjusting the pH of the mixture and/or a surfactant. If a base and/or a surfactant is included in the liquid mixture, they are preferably included within a buffer solution. Exemplary bases for use in the present invention include sodium hydroxide, triethanolamine, and choline. Exemplary surfactants for use in the present invention include sorbitan monooleate, polyethylene glycol-co-polypropylene glycol, Tween 20 and Tween 80.

The gelling material may also include combinations of materials. For example, in one exemplary embodiment the occluding hydrogel of the current invention comprises two Thiole precursors, such as, for example Pentaerythritol Tetrakis 3' Mercaptopropionate (QT) and Dithiothreitol (DTT); three Acrylate precursors, such as, for example Polypropylene Glycol Diacrylate (PPODA), Polyethylene Glycol Diacrylate (PEGDA), and Pentaerythritol Triacrylate (TA); and a Phosphate Buffered Solution with added NaOH.

As discussed above, the components can be mixed in different proportions with a one to one ratio on the functional groups to form gels with various mechanical properties and gelation periods. As is known in the art mathematical modeling may be used to predict the mechanical properties of such gels given a particular combination, as well as giving the amount of each material to add to yield specified mechanical properties.

The current invention is also directed to methods of embolizing an AVM or other type of vascular malformation in the body using the gelling material described above. Embolization. Embolization is the method of treating the AVM that involves an endovascular approach, wherein a gelling material is introduced into the AVM via a catheter, and is then injected into the complete malformation.

FIG. 1 shows a flow chart of one embodiment of a suitable method in accordance with the current invention. As shown in the flowchart, the basic method comprises several general steps, including:

Step 1: Providing separate solutions of the nucleophilic precursor component and the conjugated unsaturated precursor component along with any remaining components such as a buffer.

Step 2: Mixing the components together to form the complete gelling material.

Step 3: Introducing the Catheter to the AVM and inflating the catheter balloon to temporarily occlude the blood supply to the AVM.

Step 4: Introducing the gelling material to the AVM through the catheter.

Step 5: Maintaining the placement of the catheter until gelation of the gelling material is complete.

Once all the components have been provided and the catheter placed appropriately near the AVM, mixing to form the final precursor solution can occur in a variety of ways. Most straightforwardly, one solution contains the nucleophilic precursor component and one solution contains the conjugated unsaturated precursor component. These two components are formulated in solvent and buffer systems such that the pH and concentrations obtained after mixing are appropriate for the chemical reaction to proceed. Such mixing could occur in a static mixer at the function of two syringes, for example. Other mixing approaches can be imagined. For example, mixing can occur between fine particles of each of the two precursor solutions in an air spray.

As shown in FIG. 2A and discussed above, the precursors and buffer may be mixed prior to injection by mating the distal ends of two syringes 30 and 32. The mixture is mixed by the back and forth motion of the syringes.

Although one method of ensuring in situ gelling is discussed above, in another embodiment one solution can be prepared from both precursor components, but at a pH, for example, such that the reaction does not proceed or proceeds only slowly. After or just immediately preceding placement of the pre-mixed precursor solution, the pH can be adjusted (e.g., by change of temperature, or mixing with acid or base, or by a chemical reaction to create an acid or base, or diffusion of an acid or base), to result in a final condition in the final precursor solution that is appropriate for the chemical reaction to proceed.

Another approach is to prepare the final precursor solution at a temperature such that the reaction does not proceed or proceeds only very slowly, either related to the activation energy of the reaction or to a buffer with temperature-sensitive characteristics or both. Upon warming or cooling (most usefully warming) to the final application temperature (e.g., to body temperature after injection), the conditions in the final precursor solution are appropriate for the chemical reaction to proceed.

Figure 2:
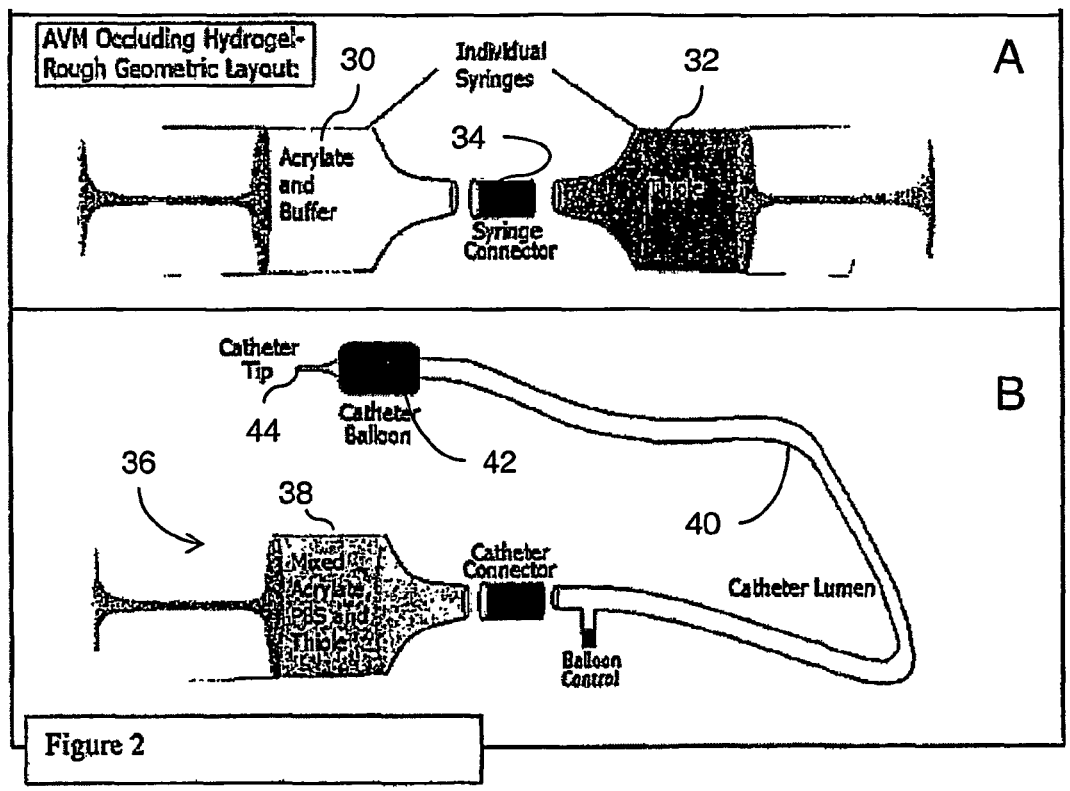
FIGS. 2A and 2B, show a schematic layout of one embodiment of a system for using an in situ occluding gelling material and its delivery system in accordance with the current invention.

Regardless of how the mixture is made, as shown in both FIGS. 1 and 2, the liquid mixture containing the nucleophilic component and the component containing a conjugated unsaturated bond is introduced into the region of the AVM in the patient using a catheter. In one embodiment, as shown in FIG. 2B, after the appropriate mixing time, a syringe 36 containing all of the mixture 38 is attached to a single lumen catheter 40 with a balloon 42 at the distal end. The catheter is placed in the region that is to be occluded, and the balloon inflated to block blood flow through the AVM while the gelling material 38 is being introduced through the outlet tip 44 of the catheter. A radiopaque agent, for example of chemical composition in the Barium Sulfate or Tantalum Oxide group, may be used to ensure the proper placement of the gelling material. As used herein, the term "patient" refers to human patients as well as other mammals.

Although catheters are discussed above, the liquid mixture can be introduced into the AVM of the patient by any suitable method. In a preferred embodiment a catheter is utilized. The catheter preferably has a size no greater than about 5 French so that it fits within the vascular system near the AVM. The catheter would desirable include a backstop mechanism, such as a balloon, to prevent backflow of the liquid mixture into the vascular system prior to gelling.

Once introduced into the body, the mixture then gels within the AVM to form a gelled composition that occludes or blocks the blood flow to the AVM. In accordance with this step of the inventive method, the Michael-type addition reaction between the nucleophilic component and the component containing a conjugated unsaturated bond is occurring predominantly, if not entirely, in situ, or within the body. Accordingly, the rate of the Michael-type reaction desirably occurs over a clinically relevant period of time at a clinically relevant temperature and pH. Preferably gelation occurs over a period of less than about 60 minutes, more preferably less than about 30 minutes, still more preferably less than about 15 minutes, even more preferably less than about 5 minutes.

The speed at which the reaction occurs is largely a function of the pH of the reaction mixture, as well as the strength of the buffer solution employed. For example, a liquid mixture containing pentaerythritol-tetrakis(3-mercaptopropionate) (QT) and poly(ethyleneglycol)-diacrylate 570 (PEGDA) in 100 mM PBS solution at pH 7.4 reacts to form a gel in about 5 minutes. In contrast, a liquid mixture containing QT and PEGDA in 10 mM PBS solution will react in about 10 minutes if adjusted to a pH of about 9. The strength of the buffer solution is preferably sufficient to deprotanate the thiols in the liquid mixture. Preferably the liquid mixture contains a PBS solution having a strength ranging from about 1 mM to about 300 mM, more preferably from about 10 mM to about 150 mM, still more preferably from about 75 mM to about 125 mM. Preferably the pH of the liquid mixture, when it is being introduced into the body, is at least 7, more preferably from about 7 to about 12. If the liquid mixture has a pH outside of this range, the pH can be adjusted immediately before introduction into the patient by addition of a suitable base, as noted above.

If desired, the liquid mixture can further include one or more additional treatment agents relevant to the chosen procedure.

Although only a single lumen balloon catheter embolization technique was discussed above, it should be understood that the gelling material composition of the current invention can be utilized with any known embolization technique. Exemplary prior art embolization techniques are described in the following U.S. patent, the disclosures of which are incorporated herein by reference: U.S. Pat. No. 5,514,379, Weissleder, et al., Hydrogel Compositions and methods of use, May 7, 1996; U.S. Pat. No. 5,667,767, Greff, et al., Compositions for use in embolizing blood vessels, Sep. 16, 1997; U.S. Pat. No. 5,823,198, Jones, et al., Method and Apparatus for *Intravascular Embolization*. Oct. 20, 1998; U.S. Pat. No. 6,066,325, Wallace, et al., Fragmented polymeric compositions and methods for their use, May 23, 2000; U.S. Pat. No. 6,096,021, Helm, et al., Flow Arrest, Bouble Balloon Technique for Occluding Aneurysms or Blood Vessels, Aug. 1, 2000; U.S. Pat. No. 6,113,629, Ken, Hydrogel for the therapeutic treatment of aneurysms, Sep. 5, 2000; U.S. Pat. No. 6,152,943, Sawhney, Methods and apparatus for intraluminal deposition of hydrogels, Nov. 28, 2000; U.S. Pat. No. 6,245,090, Gilson, et al., Transcatheter Occluding Implant, Jun. 12, 2001; U.S. Pat. No. 6,299,619, Greene, Jr., et al., Methods for embolizing a target vascular site, Oct. 9, 2001; U.S. Pat. No. 6,312,421, Boock, Aneurysm embolization material and device, Nov. 6, 2001; U.S. Pat. No. 6,342,202, Evans, et al., Compositions for use in embolizing blood vessels, Jan. 29, 2002; U.S. Pat. No. 6,463,317, Kuckarczyk, et al., Device and method for the endovascular treatment of aneurysms, Oct. 8, 2002; U.S. Pat. No. 6,475,516, DiCosmo, et al., Drug delivery via therapeutic hydrogels, Nov. 5, 2002; and U.S. Pat. No. 6,615,193, Greene, Jr, et al. Vascular embolization with an expansible implant, Dec. 26, 2000.

Although embolization techniques alone are discussed above, it should be understood that the materials and methods of the current invention may also be used with combination therapies. Combination therapies are exactly what they suggest; a separate therapy, such as surgery is performed coincidental to the embolization procedure.

EXAMPLES

For the following examples, unless otherwise indicated, pentaerythritol-tetrakis (3-mercaptopropionate) (QT) and pentaerythritol triacrylate (TA) were both obtained from Fluka (Buchs, Switzerland). Poly(ethylene glycol)diacrylate 570 MW (PEGDA), poly(propylene glycol)diacrylate 900 MW (PPODA 900), and poly(propylene glycol-co-polyethylene glycol-co-polypropylene glycol) 3300 MW (PEP) were all obtained from Aldrich (Buchs, Switzerland). Sorbitan monooleate (SM) was purchased from Sigma (Buchs, Switzerland). All other reagents were reagent grade and all materials were used as received.

Example 1

Synthesis of Poly(ethylene glycol)hexathiol (PEGHT)

The QT (8.58 g, 17.5 mmol) was combined with 8 mL $H_2O$ and 2 mL 1N NaOH in 100 mL of tetrahydrofuran (THF). The PEGDA 570 (1 g, 1.75 mmol) was combined with 1 mg of 2,6-di-tertbutyl-p-chresol (radical inhibitor) in 10 mL di-chloromethane (DCM). The PEGDA solution was then diluted with 15 mL of THF. The diluted PEG solution was then dropwise added to the stirred QT solution. After 55 min the pH was adjusted to 7 using glacial acetic acid. To remove water, the solvent was evaporated and the product was redissolved in 100 mL of toluene. The toluene was evaporated and an additional 100 mL of toluene was added. About 13 g of sodium sulfate was added, and then the sodium sulfate was removed by filtering. Before precipitation in 10-fold excess diethyl ether, the solution was concentrated by evaporating some of the toluene. The diethyl ether was decanted and the liquid product was recovered. The product was dried under vacuum.

$^1$H-NMR (CDCl$_3$): δ=4.25 (t, 2H, —OCH$_2$CH$_2$OOC—), 3.6-3.7 (40+16H, CH$_2$CH$_2$O and C(=O)OCH$_2$C(CH$_2$—)$_3$), 2.8 (m, 8H, SCH$_2$CH$_2$COO), 2.65 (m, 8H, SCH$_2$CH$_2$COO), 1.65 (t, 3H, —CH$_2$SH) ppm.

Gel permeation chromatography (GPC): $M_n$=1300; $M_w$=1500 (THF, PEG standards).

Example 2

Synthesis of Poly(ethylene glycol)tetraacrylate (PEGQA)

The PEGDA 570 (20 g, 35 mmol) was combined with 20 mg of 2,6-di-tertbutyl-p-chresol in 10 mL DCM. This was then diluted with 90 mL THF. The NaOH (3 mL, 0.2N) and 1 mL of H$_2$O were added. The QT (1 g, 2.0 mmol) was dissolved in 40 mL of THF. The QT solution was added dropwise to the stirred PEGDA solution. After 30 min, 7 μL of glacial acetic acid was added to neutralize the reaction. The solvent was evaporated and 100 mL of toluene were added. After drying over sodium sulfate, the solution was filtered, concentrated and then precipitated using 10-fold excess diethyl ether. After precipitation the product was dried under vacuum.

$^1$H-NMR (CDCl$_3$): δ=6.4 (dd, 4H, CH$_2$=CHCOO), 6.15 (dd, 4H, CH$_2$=CHCOO trans), 5.85 (dd, 4H, CH$_2$=CHCOO cis), 4.25 (t, 2H —OCH$_2$CH$_2$OOC—), 3.6-3.7 (40+16H, CH$_2$CH$_2$O and C(=O)OCH$_2$C(CH$_2$—)$_3$), 2.8 (m, 8H, SCH$_2$CH$_2$COO), 2.65 (m, 8H, SCH$_2$CH$_2$COO) ppm.

GPC: $M_n$=2600; $M_w$=2900 (THF, PEG standards)

Example 3

Preparation of Crosslinked Biomaterials

Crosslinked materials were prepared as dispersions or reverse emulsions of precursors in modified phosphate buffered saline (PBS). The PBS, 10 mM solution, was obtained by mixing equal volumes of 10 mM PBS adjusted to pH 9 with the addition of triethanolamine or 1N NaOH, respectively.

Example 3A

As a typical procedure for 75-wt % dispersion materials, 424 mg QT and 997 mg of PEGDA 570 were combined and mixed well by vortexing. Air bubbles were removed by sonication. The PBS solution (473 mg) was added to the mixed precursors. The mixture was again vortexed for about 2 min to mix well and disperse the precursors in the aqueous solution. Following vortexing, the mixture was again sonicated to remove air bubbles. The materials were then allowed to gel at either 25° C. or 37° C.

Example 3B

Dispersion-type materials with barium sulfate inorganic particles (as a radiocontrast agent) were prepared according to the protocol described in Example 3A. Before addition of the activating buffer (pH 9.0 PBS), 10 wt % of 0.8 μm BaSO$_4$ particles were added to the mixed precursors. The activating buffer was then added, and the mixture was vortexed and allowed to crosslink.

Example 3C

SM was added to the PBS 9.0 buffer at 4 wt % before adding the mixed precursors, QT and PEGDA 570, in amounts as described in Example 3A.

Example 3D

Dispersion-type materials at 75 wt % solid were prepared as described in Example 3C using the prereacted precursors, PEGHT and PEGQA at a 1:1 thiol to acrylate ratio.

Example 3E

A reverse-emulsion material was prepared. 1223 mg QT (2.5 mmol) was mixed with 993 mg TA (3.3 mmol) and 90 mg PEP. The PBS buffer, with 0.1N NaOH, (738 mg) was added, and the mixture was vortexed thoroughly. The mixture was then allowed to crosslink.

Example 4

Hydrogel Useful For Occluding AVMS

An example of a gel useful for treating AVMs was composed of the following components in weight fraction: 0.0459984 of QT, 0.0819367 of DTT, 0 of TA, 0.6258286 of PPODA, 0 of PEGDA, and 0.25 of PBS. Where the PBS included 15 30% of a 1N NaOH solution for different gelation periods. The resulting gel met the following design specifications for mechanical properties:

Modulus (1.5+0.3 Mpa)
Fatigueability (Infinite Cycles to Failure at stresses double that of blood pressure)
Ultimate Compressive Strength (4.5 Mpa)

Example 5

Determination of Mechanical Properties

Crosslinking Kinetics-Shear Rheology

The dispersions or reverse emulsions at 75 wt % content were placed between two parallel plates (separated by 100 μm) of a CVO120 Rheometer (Bohlin Instruments) at 25° C. A constant oscillatory strain of $3\times10^{-1}$ at 1 Hz was applied. The gel point was defined as the time when the phase angle was equal to 45° (i.e., loss modulus equal to the storage modulus). The mean gel time and mean rate of change in the phase angle at gelation for five samples were determined for each of these three materials.

Cross-Linking Kinetics-Attenuated Total Reflection-Infrared Spectroscopy (ATR-IR)

The QT and PEGDA (75 wt %) dispersion gels were prepared with 1:1 thiol to acrylate ratios and 2:1 ratios to demonstrate the 1:1 consumption of thiols and acrylates by quantifying the S—H stretching vibration at 2600 cm$^{-1}$ and the olefin out-of-plane C—H bending vibration at 800 cm$^{-1}$.

Both peaks were normalized in intensity, referring to the peak of C—H stretching vibrations, the intensity of which should not change dramatically during the reaction.

Morphology

The physical morphology of 75 wt % QT/PEGDA dispersions and QT/PPODA reverse emulsions was investigated using scanning electron microscopy (SEM) on a JEOL 255 electron microscope. Dispersion materials (75 wt % solid) were also imaged using light microscopy at 100× in bright field.

Mechanical Properties

Mechanical properties in compression were investigated for dispersion-type materials with and without added surfactant or radiopaque inorganic particles, for dispersion-type materials using prereacted precursors, and for reverse emulsion-type materials. The effect of the thiol-to-acrylate ratio on material ultimate strength and ultimate deformation was also investigated in the dispersion materials by adjusting the relative quantities of QT and PEGDA 570, keeping the solid content at 75 wt %.

Mechanical properties were evaluated for the reverse emulsion-type materials, varying the solid content and the crosslinking density (by substituting TA and PPODA 900).

Each gelling mixture was poured into polyethylene tubes with 8 mm i.d. and allowed to cure for 24 h. Following gelation, the material was cut into 6-mm-long sections, using a metal frame to standardize the sample size and ensure sectioning perpendicular to the axis of the cylindrical sample. After 24 h in 10 mM PBS, the gels were compressed with a Zwick Z005/TN2S mechanical tester (Zwick GmbH, Ulm, Germany) with a 5 kN load cell at 10 mm/min to gel $\sigma_{max}$ (ultimate strength) and $\delta_{max}$ (ultimate deformation) data. At least three samples for each material type were tested.

The addition of SM decreased the gel point from 9.4±0.6 min. to 6.4±0.4 min (n=3, p=0.001). The reverse-emulsion material showed an even shorter gel point, 4.9±0.8 min, but with a more gradual transition: d(phase angle)/dt of only 12±3°/min compared with 57±4°/min (for dispersion-type materials without SM) or 83±6°/min (dispersion-type materials with SM).

Monitoring the depletion of thiols and acrylates as a function of time showed that both with 1:1 and 2:1 thiol-to-acrylate formulations the two groups followed similar depletion kinetics. Additionally, at 1:1 ratio, no unreacted groups were visible at the end of the reaction, whereas in the 2:1 case the thiols were reduced to half their original concentration, whereas the acrylates were reduced to nearly zero at the end of the reaction.

The SEM images showed the course and likely interpenetrated structure of the dispersion materials, and the continuous organic phase of the reverse-emulsion ones.

From compression stress-strain curves, the ultimate strengths and ultimate deformations were determined at 75 wt % solid content. For the dispersion material, ultimate strength of 1.8±0.2 MPa and ultimate deformation of 35±2% were observed. An increase in the ultimate deformation was noted upon the use of an emulsifier, probably because of the higher homogeneity of the sample; apparently the use of prereacted precursors or the addition of the inorganic radiopaque material did not improve the stability of the dispersion as much as the emulsifier. In the corresponding reverse emulsion-type material the continuous organic phase gave a much stronger material (6.7±0.5 MPa ultimate strength) while demonstrating a similar ultimate deformation (37±2%).

For reverse-emulsion materials the ultimate strength, ultimate deformation, and Young's modulus increased with increased solid content or increased crosslinking density seen by exchanging a higher-molecular-weight precursor, PPODA 900 with the low-molecular-weight TA.

Example 6

Mathematical Modeling of Stabilization Properties of Embolization Using In Situ Gelling Material In this Example the extent to which the risk of rupture and hemorrhage is reduced by the addition of the inventive embolization material to an AVM is determined. In determining the stresses exerted on and by the embolization material, we have assumed a cylindrical geometry for the material. Although this assumption is not physiologically accurate as there are many convolutions and general anatomical tapering within the AVM nidus, the convolutions and tapering of the AVM will oppose the stress exerted on the arterial side of the embolization material in the form of a gradient of frictional forces acting on the material in the opposite direction of the blood pressure stress. The maximal stress would appear at the arterial end of the material, and would equal the stress being applied by the blood pressure. The stress in the remainder of the material would drop in proportion to the frictional force gradient. By assuming a cylindrical material, the maximal stress exerted on the material will be transmitted throughout the entire geometry; therefore, the cylindrical geometry becomes a worst-case scenario.

The cyclic beating of the heart exerts a maximum pulsatile stress on the vessel walls on the arterial side of an AVM ($\sigma_{BP}$) equal to the arterial feeder pressure ($P_{AF}$). This cyclic stress applied to the biomechanically abnormal vessels of an AVM is the source of AVM vessel rupture and subsequent brain hemorrhaging. Mean systemic arterial pressures are generally in the range of 9.3 to 10.7 kPa (70-80 mmHg), with extremely hypertensive mean systemic pressures approaching 19.2 kPa (144 mmHg). Assuming a linear relationship between the systemic arterial pressure and the arterial feeder pressure, arterial feeder pressures are normally in the range of 5.3 kPa (40 mmHg), but can reach values as high as 12 kPa (90 mmHg) for very high systemic hypertension. When this axial stress ($\sigma_{BP}$) is applied to the embolization material a compressive strain ($\epsilon_z$), inversely proportional to the elastic modulus of the material ($E_G$), arises in the direction of the flow.

$$\varepsilon_Z = \frac{\sigma_{BP}}{E_G} = \frac{P_{AF}}{E_G} \quad (1)$$

This compression of the material will result in a radial stress ($\sigma_r$) exerted on the vessel walls from the material. This radial stress is a function of the elastic properties of both the material and the vessel wall. If the elastic modulus of the vessel was zero (no vessel present), the radial deformation of the material could be described using the Poisson's ratio relationship:

$$\epsilon_o = \upsilon \times \epsilon_z \quad (2)$$

where $\upsilon$ is the Poisson's ratio of the material. In this case, all of the energy of the material would be released in the radial expansion, and none of the energy would be exerted on the zero modulus "vessel". On the other extreme, if the elastic modulus of the vessel was infinite, the material could not deform in the radial direction, and all of the energy of the compressed material would be exerted on the vessel. In this case, the stress exerted on the vessel wall could also be explained using the Poisson's ratio:

$$\sigma_r = \upsilon \times P_{AF} \quad (3)$$

For a static situation, the radial stress experienced by the material and the circumferential stress exerted on the vessel can be set equal to one another, yielding a more general description of the radial stress and displacement for a vessel modulus between zero and infinity:

$$\sigma_r, E_G \times (\epsilon_o - \epsilon_r) = E_v \times \epsilon_r \quad (4)$$

where $\epsilon_r$ is the actual radial displacement, and $\epsilon_o$ is the radial displacement without a constricting vessel, as given in equation (2). Solving for $\epsilon_r$ we find:

$$\varepsilon_r = \frac{E_G \times \varepsilon_0}{E_v + E_G} \quad (5)$$

By substituting equation (5) for $\epsilon_r$ in equation (4), equation (2) for $\epsilon_o$ in equation (4), and equation (1) for $\epsilon_z$ in equation (2), we find:

$$\sigma_r = \frac{E_v \times \upsilon \times P_{AF}}{E_v + E_G} \quad (6)$$

Therefore, the radial stress in the material and the circumferential stress in the vessel is a function of the vessel and material properties, as well as the arterial feeder blood pressure. In order to predict the response of the tissue to the material, then we must first predict the properties of the material. The elastic modulus of the material ($E_G'$) can be found using the following equation:

$$E_G' = 2 \times (1+\upsilon) \times G_G \quad (7)$$

where $\upsilon$ is the Poisson's ratio of the material, and $G_G$ is the shear modulus of the material. Due to the rubbery behavior of the materials, the Poisson's ratio was assumed to be constant, with a value of 0.5; nevertheless, model simulations were performed for an extremely low value of 0.25 to test the sensitivity of the model.

The value of $G_G$ is unknown, and another relationship must be made relating the shear modulus to the cross-link density of a material:

$$G_G = \rho_x \times R \times T \quad (8)$$

where R and T are given input values (Gas Constant and Temperature Kelvin respectively), and $\rho_x$ is the overall cross-link density of the material, which can be expressed as:

$$\rho_x = \frac{\rho}{M_c} \quad (9)$$

where $\rho$ is the density of the material and $M_c$ is the average molecular weight between cross-links.

The material density can be predicted as the weight average of the densities of the precursors and PBS used to create the material. The $M_c$ of the material can be found using the following relation:

$$M_c = \frac{M_n}{(1+v_e)} = \frac{\sum_{i=1}^{\infty}(n_i \times M_{Wi})}{\sum_{j=1}^{\infty}\left(\frac{f_j}{2} \times m_j\right)} \quad (10)$$

where $M_{Wi}$ is the molecular weight of the material of the $i^{th}$ precursor, $n_i$ is the number of moles of the $i^{th}$ precursor, $f_j$ is the functionality of the $j^{th}$ precursor with functionality of at least three, $m_j$ is the number of moles of the $j^{th}$ precursor with functionality of at least three, and $v_e$ is the effective number of cross-links per original chain. For stoichiometry, the number of moles of each precursor is constrained by the following equality:

$$\sum_{i=1}^{\infty}(n_{i(thiols)} \times f_{i(thiols)}) = \sum_{i=1}^{\infty}(n_{i(acrylates)} \times f_{i(acrylates)}) \quad (11)$$

Equations 7-10 can then be combined to form an expression for the elastic modulus of the material:

$$E_G' = 2 \times (1+\upsilon) \times \left(\frac{\rho}{M_c}\right) \times R \times T \quad (12)$$

This prediction of the elastic modulus of the material assumes an unrealistic 100% material composition, i.e., no buffer or PBS content. Our material configuration follows a reverse emulsion Michael-type reaction and the mechanical properties of the cross-linked phase dominates those of the water phase (PBS). The PBS becomes equivalent to pores within a matrix. A more appropriate expression for a porous material modulus follows the following relation[18]:

$$E_G = E_G' \times (1 - 1.9 \times V + 0.9 \times V^2) \quad (13)$$

where V is the volume fraction of the pores in the material.

With a prediction for the mechanical properties of the material, we reverted to an electrical network model created by Hademenos and Massoud to assess the risk of rupture of vessels within an AVM, the disclosure of which is incorporated herein by reference. (Hademenos, G. J., T. F. Massoud, "An electrical network model of intracranial arteriovenous malformations: analysis of variations in hemodynamic and biophysical parameters", *Neur. Res.*, 18:575-589, 1996.) In short, the rupture prediction model is developed by setting two expressions of the circumferential stress in the vessel equal to one another:

$$S_1 = \frac{P \times R}{t} = S_2 = \varepsilon_\theta \times E_v \quad (14)$$

where $S_1$ is the Hoop stress, $S_2$ is the Lagrange/Piola stress, P is the pressure in the vessel, R is the vessel radius, t is the vessel thickness, $\epsilon_\theta$ is the circumferential vessel strain, and $E_v$ is the elastic modulus of the vessel. Taking the differential of the strain, and defining the volume distensibility of a vessel as dV/dP, yields the expression:

$$\frac{dV}{dP} = \frac{(2 \times \pi \times R \times L) \times \left[\frac{R}{t} - \left(\frac{P \times R}{t^2}\right) \times \frac{dt}{dP}\right]}{\frac{E_v}{R} - \frac{P}{t}} \quad (15)$$

Making a zero order approximation, a critical radius can be defined at which a disruption of state variables could possibly induce rupture.

$$R_c = \frac{E_v \times t}{P} \quad (16)$$

By evaluating the functional distribution of the critical radius with respect to pressure extremes and assuming $E_v$ and t are constant, an expression for the risk of AVM rupture can be derived.

$$\text{Risk} = \frac{\ln\left\{\frac{P_{exp}}{P_{min}}\right\}}{\ln\left\{\frac{P_{max}}{P_{min}}\right\}} \quad (17)$$

For $P_{max}$ and $P_{min}$, one can assume values of central venous pressure and "maximal intranidal pressure" of 9.9 kPa (74 mmHg) and 670 Pa (5 mmHg), respectively. Meanwhile, the constant $E_v$ and t values were assumed to be 5 kPa and 50 μm. Then adjustments are made to the risk prediction to account for variations of $E_v$ from 1 to 10 kPa, and variations of t from 20 to 70 μm to yield:

$$\text{Risk} = \frac{\ln\left\{\frac{P_{exp}}{P_{min}}\right\} \times 2 \times E_{vtyp} \times t_{typ}}{\ln\left\{\frac{P_{max}}{P_{min}}\right\} \times 2 \times E_{vmax\,or\,min} \times t_{max\,or\,min}} \quad (18)$$

This expression can then be used to theoretically determine the risk of AVM rupture for AVMs without embolization with the inventive gelling material. We wish to utilize this model to theoretically predict the risk of rupture for individual AVM vessels that have been embolized with our material. Utilizing our prediction of the circumferential stress exerted on the vessel in equation 6 and the Poisson's ratio expression in equation 3 with $P_{exp}$ replacing $P_{AF}$, $P_{exp}$ can be determined by:

$$P_{exp} = \frac{\sigma_r}{\upsilon} = \frac{E_v \times P_{AF}}{E_G + E_v} \quad (19)$$

Material Preparation

The material was formed by cross-linking three multi-functional precursors: pentaerythritol-tetrakis(3-mercapto-propionate) 489 MW (QT), a tetrafunctional thiol precursor; poly(propylene glycol)diacrylate 900 MW (PPODA), a bifunctional acrylate precursor; and 1,4-Diothio-DL-threitol 154 MW (DTT), a bifunctional thiol precursor. QT was obtained from Fluka (Buchs, Switzerland), and both PPODA and DTT from Aldrich (Buchs, Switzerland). All other reagents were reagent grade and we used all materials as received.

TABLE 1

| COMPRESSION TEST SAMPLE TARGET WEIGHTS | | | | | | | |
|---|---|---|---|---|---|---|---|
| Group 1 ($DTT_f = 0$, $QT_f = 1.0$) | | Group 2 ($DTT_f = .1$, $QT_f = 0.9$) | | Group 3 ($DTT_f = .2$, $QT_f = 0.8$) | | Group 4 ($DTT_f = .3$, $QT_f = 0.7$) | |
| QT | 602 mg | QT | 544 mg | QT | 486 mg | QT | 428 mg |
| DTT | 0 mg | DTT | 40 mg | DTT | 76 mg | DTT | 116 mg |
| PPODA | 2213 mg | PPODA | 2224 mg | PPODA | 2234 mg | PPODA | 2244 mg |
| PBS | 940 mg | PBS | 936 mg | PBS | 932 mg | PBS | 929 mg |
| Group 5 ($DTT_f = .4$, $QT_f = .6$) | | Group 6 ($DTT_f = .5$, $QT_f = 0.5$) | | Group 7 ($DTT_f = .6$, $QT_f = 0.4$) | | | |
| QT | 368 mg | QT | 308 mg | QT | 248 mg | | |
| DTT | 154 mg | DTT | 194 mg | DTT | 234 mg | | |
| PPODA | 2255 mg | PPODA | 2266 mg | PPODA | 2270 mg | | |
| PBS | 924 mg | PBS | 922 mg | PBS | 920 mg | | |

Cross-linked materials were prepared as reverse emulsions of precursors in modified PBS. The PBS was adjusted, 100 mM solution, to pH 13.0 with the addition of 1N NaOH. Thiol and acrylate precursors were always mixed in a 1:1 thiol to acrylate ratio to achieve stoichiometry. Seven sample groups were then prepared with unique DTT and QT functional end mole fractions (see Table 1, above). $DTT_f$ and $QT_f$ represent the number of thiol functional ends contributed by DTT or QT divided by the total number of thiol functional ends, respectively. The weight of each precursor was determined by the stoichiometric condition in equation (11) for a total material volume of 3.6 mL. The PBS weight percent for all samples was held constant at 25%.

The appropriate weights of DTT, QT, PBS, and PPODA were then combined in 10 mL syringes and air bubbles were removed by inverting the syringe and advancing the plunger until only the precursors and PBS remained. The precursors were mixed for two minutes by a back-and-forth motion of the syringe plungers. After two minutes, the syringes were deteched and an excess of the mixture was pushed into a mold. After the mixture had finished cross-linking, the excess material was removed by running a stainless steel razor blade along the top of the mold.

Compression Tests

A total of 36 cylindrical compression test samples: each 0.63±0.01 inches in diameter were then prepared. With the exception of Group 7, four samples in each group were 0.25±0.01 inches in length and one sample in each group was 0.125±0.01 inches in length. Group 7 had four 0.25-inch samples and two 0.125-inch samples. The shorter samples were included to verify that the modulus was not significantly altered by a change in length of the compression sample.

The compression tests were performed on an MTS Sintech 1/S mechanical tester (Research Triangle Park, N.C.) that compressed the samples at a rate of 0.1 inches per minute. The elastic modulus of each sample was determined from the slope of a linear regression that was fit to at least 40 data points between 25 kPa and 500 kPa, with $R^2>0.975$.

Model Modulus Simulations

The above-discussed model was then used to predict the cross-link density and elastic modulus of the material, and model results compared to the compression testing empirical results for the elastic modulus. $DTT_f$ and $QT_f$ data was input into the model for each of the seven groups, and the cross-link density ($\rho_x$) and volume fraction elastic modulus ($E_G$) output recorded for each simulation. The modulus efficiency was then calculated for each group mean as the mean divided by the model prediction. Variations were also simulated in the Poisson's ratio from 0.25 to 0.5 to identify any model discrepancies that may have resulted from an inappropriate Poisson's ratio assumption.

Figure 3:
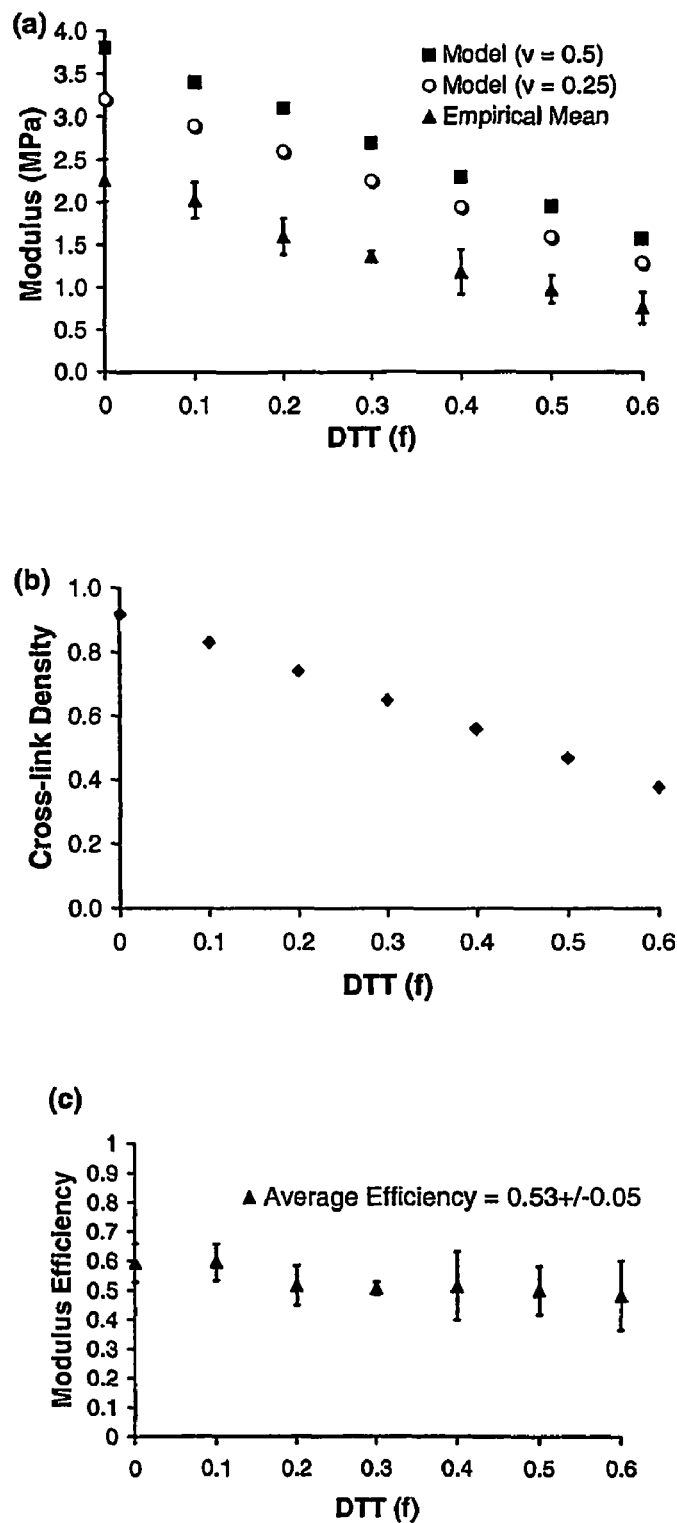
FIGS. 3A to 3C, graphical data plots of model and experimental modulus calculations (3A), cross-link density (3B), and modulus efficiency (3C) versus $DTT_f$.

FIG. 3A displays data for both the model and experimental modulus calculations. The experimental mean for each group of samples was plotted after excluding four individual outliers (standard residual>2.0) that were identified from a linear regression of the modulus versus $DTT_f$. To verify that including the 0.125-inch samples in the calculation of the mean modulus, a paired T-test was performed to compare groups with the shorter samples to the same groups the shorter sample excluded. There was no significant difference in the groups when the shorter samples were included (p>0.50). Error bars represent ±1 standard deviation (S.D.). Two model modulus predictions are displayed: $\upsilon=0.5$ and $\upsilon=0.25$. The area between the model estimate curves represents the potential error in the model prediction as a result of an inappropriate Poisson's ratio estimate.

FIG. 3B illustrates the model prediction for the cross-link density of the material as a function of $DTT_f$. A linear regression fit to the cross-link density predictions follows the following equation:

$$\rho_x = 0.92 + 0.90 \times DTT_f \quad (20)$$

The cross-link density intuitively drops to near zero when $DTT_f$ equals 1.0. The quantity of tetrafunctional QT groups drops to zero and only bifunctional acrylate and thiol groups remain; hence, there is no cross-linking for $DTT_f=1.0$.

FIG. 3C displays the modulus efficiency as a function of $DTT_f$, where modulus efficiency is defined by the following relation:

$$\eta_m = \frac{E_{G(experimental)}}{E_{G(model)}} \quad (21)$$

where $\eta_m$ is the modulus efficiency of the group, $E_{G(experimental\ mean)}$ is the mean experimental modulus of the group, and $E_{G(model)}$ is the model prediction for $\upsilon=0.5$. The error bars represent ±1 S.D. The modulus efficiency was approximately constant with a value of 0.53±0.05 (53±5%).

Figure 4:
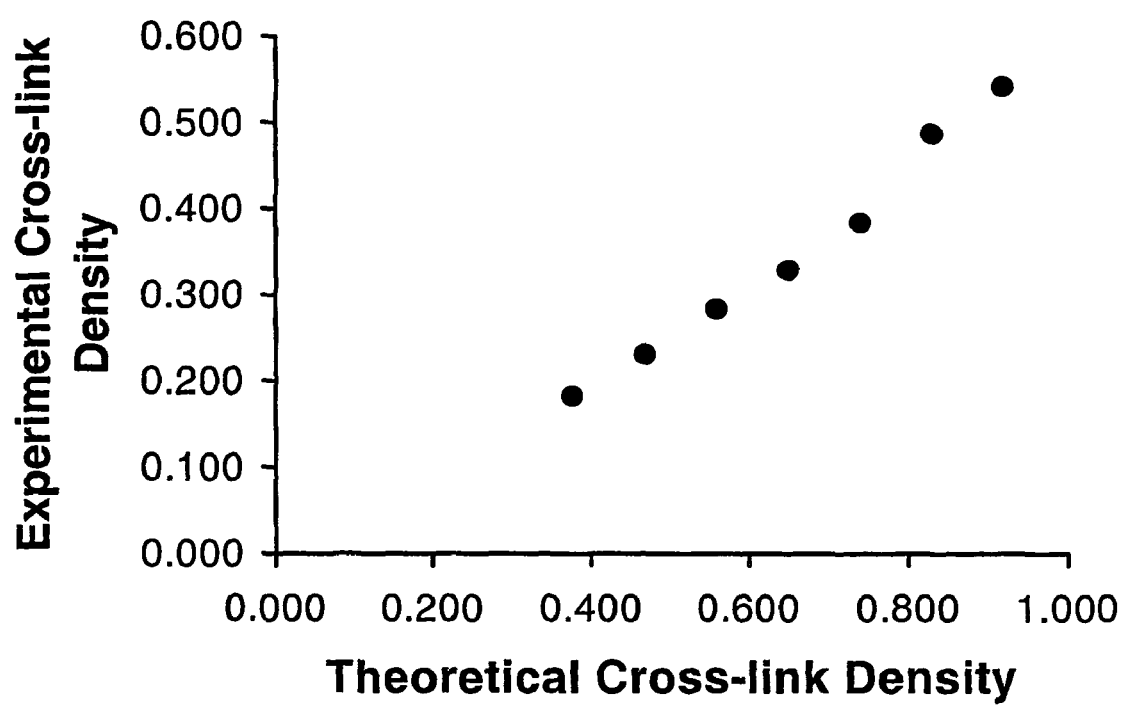
FIG. 4, graphical data plot of experimental cross-link density as a function of theoretical cross-link density.

Cross-linking efficiency has been identified as the main contributor to elastic modulus inefficiency in conventional hydrogels. Experimental cross-link densities ($\rho_{xe}$) are consistently lower than theoretical cross-link densities ($\rho_{xt}$), and follow a basic linear relationship:

$$\rho_{xe} = \alpha + \beta \times \rho_{xt} \quad (22)$$

where $\alpha$ is the experimental cross-link density induced by polymer chain entanglements without chemical cross-linking and $\beta$ is the cross-linking efficiency. Cross-linking efficiency is strongly dependent on the cross-linking agent. Studies show variations in cross-link efficiency from 0.0066 for N,N-methylenebisacrylamide (NMBA) to 0.82 for poly(2-hydroxyethyl methacrylate) (PHEMA) cross-linked with ethyleneglycol dimethacrylate (EDMA)[3,20]. FIG. 4 presents data for experimental cross-link density as function of theoretical cross-link density. Experimental cross-link densities were calculated by performing an inverse simulation on the model using equations 7, 8, and 13.

As shown in FIG. 4, the experimental modulus for the Michael-type cross-linked material of the current invention was consistently 53±5% of the modulus predicted by the theoretical mathematical model for a Poisson's ratio of 0.5. A linear regression to the data presented in FIG. 5 yielded $\alpha=-0.086\pm0.07$ and $\beta=0.67\pm0.1$ for 95% confidence intervals ($R^2=0.98$). The fact that the cross-linking efficiency is approximately the same as the modulus efficiency suggests that most, if not all, of the loss in modulus efficiency can be accurately attributed to a loss in cross-linking efficiency. The fact that $\alpha \approx 0$ also suggests that the precursor chains are small enough that entanglement effects on elastic modulus are negligible.

Non-stoichiometry of reaction increases the number of unreacted functional groups of the excess precursor, and may also add to the effect of the cross-link inefficiency. Because of the high density and tetrafunctional nature of QT, non-stoichiometry is most affected by fluctuations in the weight of QT added for the reaction. The QT sensitivity is augmented as $DTT_f$ increases because the absolute quantity of QT added is decreased for higher $DTT_f$ values. Hence, the slight decline in modulus efficiency as $DTT_f$ increases (see FIG. 3).

Reduction in Circumferential Stress

The circumferential vessel stress, defined in equation 6, was calculated and plotted using the empirically deduced mean modulus of each of the seven groups and normal physiological parameters as defined by Hademenos and Massoud. The material configuration was then identified with the greatest reduction in circumferential stress and the remainder of the sensitivity and risk analysis was performed using the mean empirical modulus for that configuration.

Figure 5:
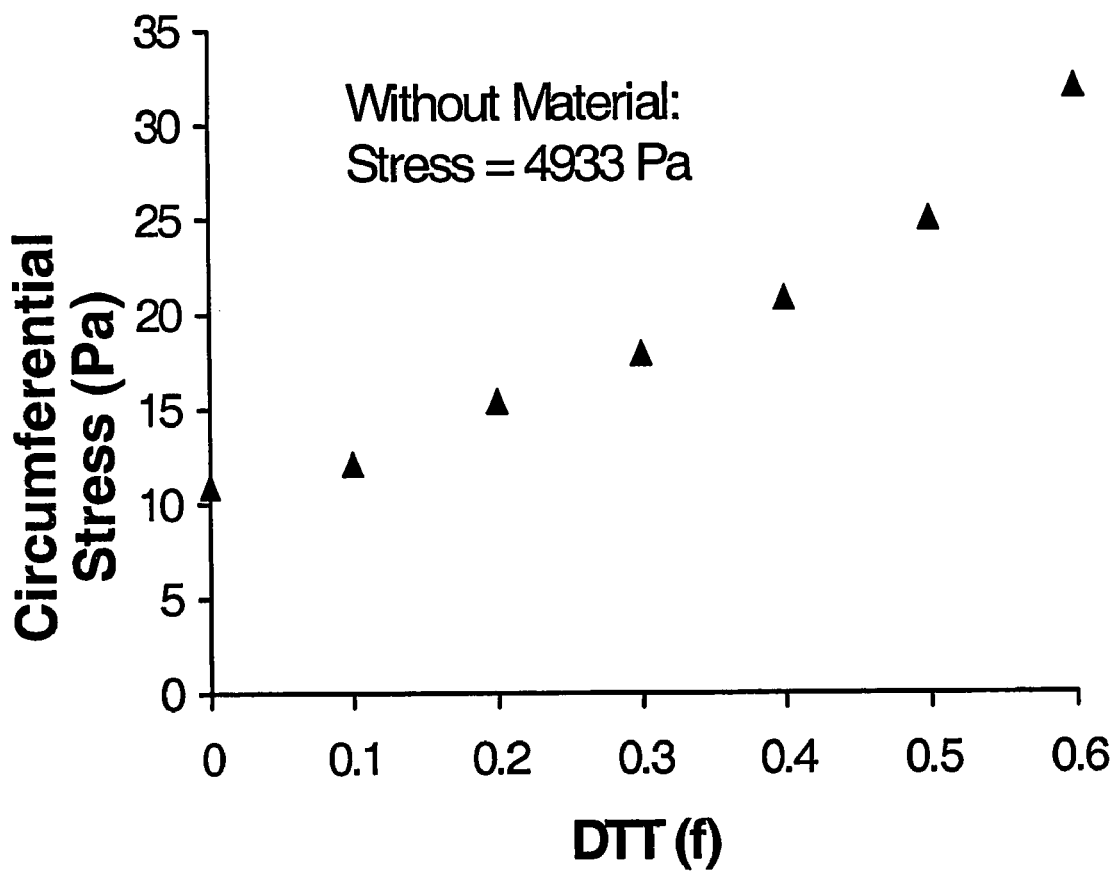
FIG. 5, graphical data plot of circumferential stress exerted on the AVM vessel from a physiologically normal stimulus prior to and after embolization, as a function of $DTT_f$.

FIG. 5 demonstrates the reduction in circumferential stress exerted on the AVM vasculature by the addition of the embolization material of the current invention. The stress is reduced from 4933 Pa without an embolization material to the values shown in FIG. 2 for the various groups. The maximal reduction of stress is seen in the material configuration where $DTT_f=0$, where only 10.9 Pa are exerted on the vasculature.

Rupture Risk

The risk of rupture as defined by equations 18 and 19 was also calculated. Due to the mathematical nature of the rupture risk calculation, it is possible to calculate risks greater than 100% or less than 0%[6]. Risks above 100% or below 0% were set equal to 100% or 0%, respectively. The risk of rupture for both AVMs that had been occluded and those that had not were calculated for comparison. To identify the changes in rupture risk due to variations in vessel stiffness ($E_v$), the rupture risk was calculated for variations of $E_v$ from 100 Pa to 600 kPa while holding other parameters at normal physiological conditions[7]. For this analysis, the varied $E_v$ parameter was substituted for $E_{v\ max\ or\ min}$ in the denominator. The value $t_{min}$=20 µm was also included in the denominator as a worst case estimate. To identify the changes in rupture risk due to variations in arterial feeder blood pressure ($P_{AF}$), the rupture risk was calculated for variations in $P_{AF}$ from 0.5 to 12 kPa (3.75 to 90 mmHg) while holding other parameters at normal physiological conditions[6]. The value $P_{AF}$ for $P_{exp}$ was also calculated for the case where no material was present and included $t_{min}$=20 µm and $E_{v\ min}$=1 kPa in the denominator as worst case estimates.

Figure 6:
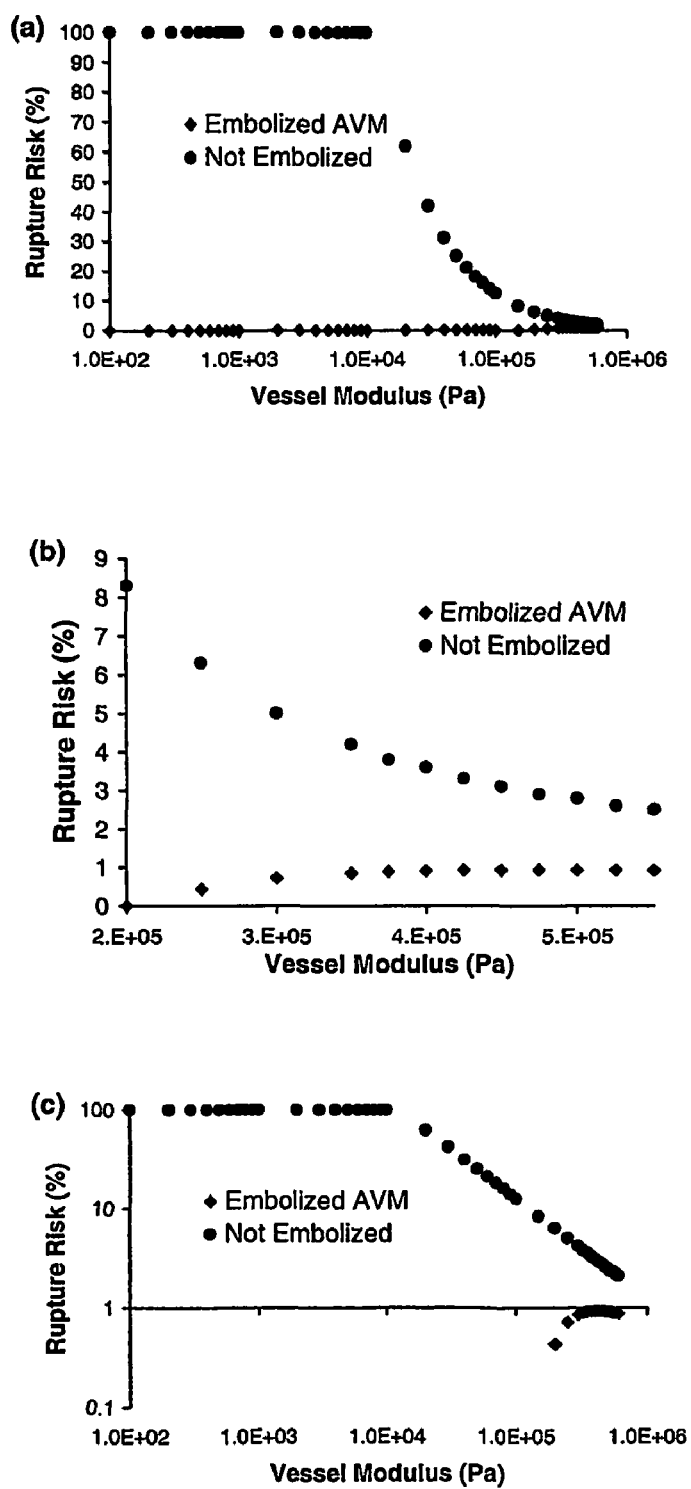
FIGS. 6A to 6C, graphical data plots of theoretical risk of rupture as defined in equation 19 versus vessel modulus for both embolized and non-embolized AVM vessels (3A), an expanded view of the data present in 3A for variations in vessel modulus from 200 kPa to 500 kPa (3B), and a log-log scale version of 3A (3C)

FIG. 6A illustrates the theoretical risk of rupture for embolized and non-embolized AVM vessels for variations in vessel modulus from 100 Pa to 600 kPa. The vessel modulus is plotted on a log scale to account for the magnitude of modulus variation. The theoretical risk of rupture for non-embolized AVM vessels was 100% for $E_v$<10 kPa. For greater vessel moduli, the non-embolized risk decreased logarithmically (as can be seen in the log-log plot in FIG. 6C). The embolized vessel risk is indistinguishable in FIG. 6A because of poor resolution induced by the large scale.

FIG. 6B is an expanded view of the theoretical rupture risk for variations in vessel modulus from 200 kPa to 500 kPa. The logarithmic decrease in risk for non-embolized AVM vessels is still apparent. A positive risk for embolized AVM vessels can also be seen for $E_v$>165 kPa. The risk for embolized AVM vessels reaches a maximum of 0.93% at $E_v$=421 kPa.

FIG. 6C is a log-log scale version of FIG. 5A and demonstrates the direct logarithmic nature of the decrease in non-embolized vessel rupture risk. The maximum embolized vessel modulus at 421 kPa can also be seen.

Figure 7:
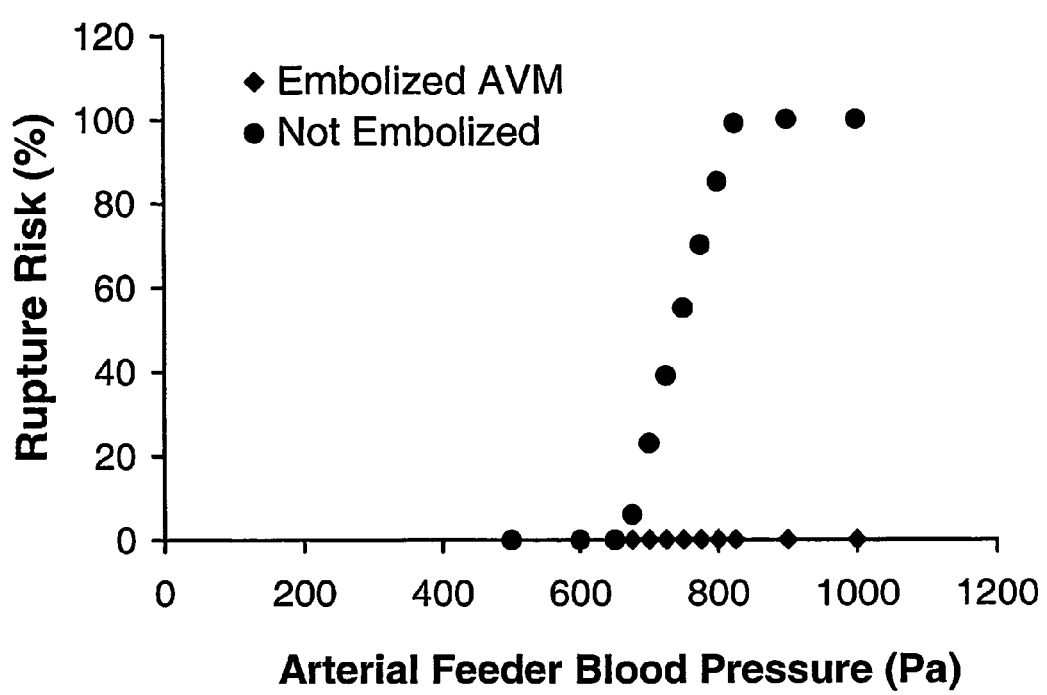
FIG. 7, graphical data plot of theoretical risk of AVM vessel rupture for both embolized and non-embolized vessels as a function of intravascular blood pressure.

The risk of rupture for embolized vessels remained zero throughout the range of blood pressure simulations from 0.5 to 12 kPa. Rupture risk for embolized vessels does not become positive until the blood pressure reaches 302 kPa (2265 mmHg), a pressure orders of magnitude above maximal physiological AVM intravascular pressures. FIG. 7 shows the risk of AVM vessel rupture for both embolized and non-embolized vessels for variations in AVM vessel blood pressure from 500 to 1,000 Pa. For pressures below 650 Pa (4.9 mmHg), the risk of rupture for non-embolized AVM vessels is zero. For pressures above 825 Pa (6.2 mmHg), the theoretical risk of rupture is 100%. A sharp increase in risk is seen for pressures between 650 and 825 Pa. It should be noted that the reason the risk of rupture is 100% for small blood pressures (6.2 mmHg) is because of the worst-case estimates used for $t_{min}$ and $E_{v\ min}$ in the rupture risk calculation.

As shown in the Figures, the risk of AVM vessel rupture is reduced dramatically over physiological ranges of vessel modulus, thickness, and blood pressure by the addition of the embolization material of the current invention. Specifically, as the vessel modulus decreases over physiological ranges, the risk of non-embolized vessel rupture increases while the risk of embolized vessel rupture decreases. This phenomenon arises from the balance of forces that is described in equations 2, 3 and 4.

To account for changes in nonlinearity in vessel elasticity and for vessel modulus values out of the ranges assumed by Hademenos and Massoud, the vessel modulus has been varied over a range of 100 Pa to 600 kPa. Throughout this range of modulus values, the risk of rupture for embolized AVM vessels is well below the risk of rupture for non-embolized vessels.

The log-log plot in FIG. 6C illustrates the first-order low-pass filter behavior of the vessel rupture risk for the non-embolized vessels as a function of vessel modulus. The logarithmic decrease is analogous to a −20 dB/decade drop in systems theory. The plot in FIG. 6C also illustrates a rapid rise in the risk of rupture for embolized vessels to a maximum of 0.93% at $E_v$=421 kPa.

In conclusion, an AVM embolization gelling material has been developed and described. Empirically determined elastic moduli for various material compositions ranged from 0.76 to 2.26 MPa. The theoretical risk of AVM rupture, as defined by Hademenos, et al., using the exemplary materials was reduced to below 1.0% for all parameter variations. A reduction in the circumferential stress experienced by the vessels in the AVM on the order of two orders of magnitude was also predicted by the model. Material modulus means averaged 53±5% of the modulus predictions for the same groups of materials, while the cross-linking efficiency was identified as β=0.55.

Example 7

In Vivo Embolizations in Swine

A material configuration with $DTT_f$=0 was selected to perform in vivo embolizations on swine rete mirabile AVM models. A model AVM was prepared in five porcine (rete mirabile) and then embolized with an exemplary in situ-gelling, water-borne material based on pentaerythritol tetrakis-3 mercaptopropionate and poly propylene glycol diacrylate (~900 g/mol).

Figure 8:
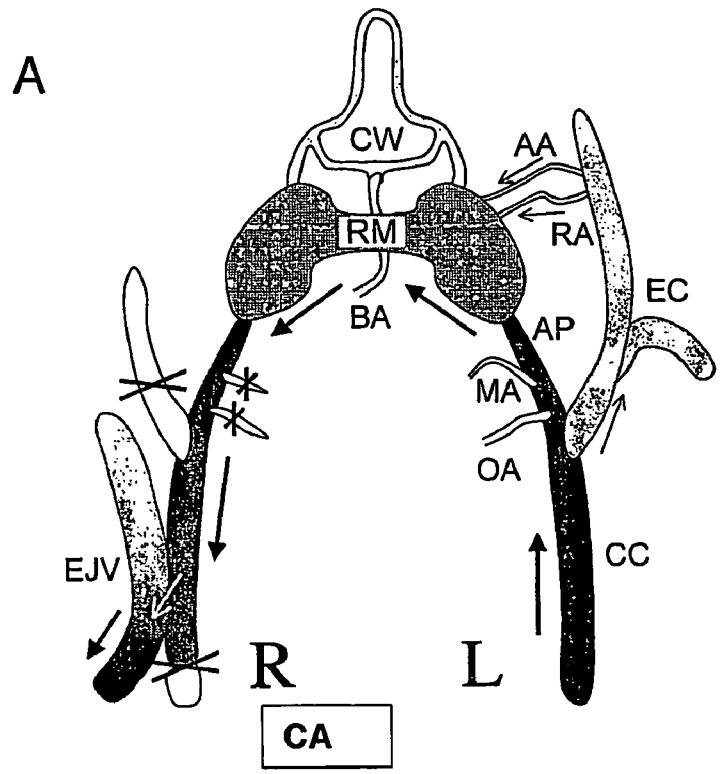
FIGS. 8A and 8B, schematic diagrams of the swine rete vessels and the resulting vessel model in a unblocked (8A) and blocked or occluded state (8B)
Figure 8:
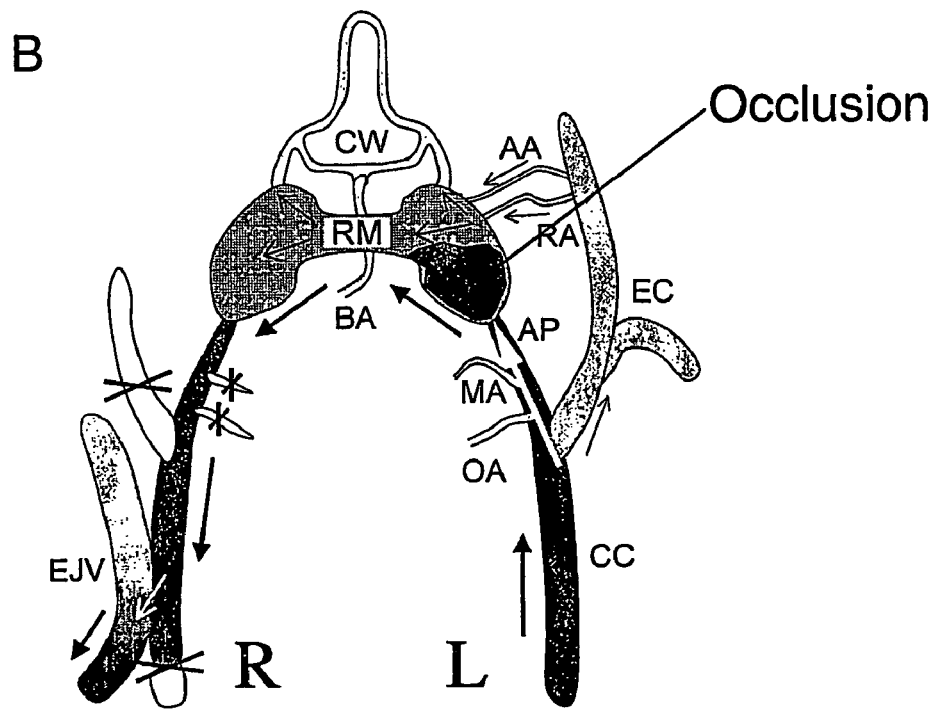

As shown in FIGS. 8A and 8B, the swine vasculature of the head and neck includes carotid arteries (CA) on both sides of the neck as well as adjacent jugular veins (EJV). The CA travel into the base of the skull, and the ascending pharyngeal (AP) arterial branch of the CA leads to a complex vasculature on each side of the neck and skull called the rete mirabile (RM). The AVM model is created by reversing flow through the right side of the RM, resulting in a flow loop through the base of the skull and brain. This is accomplished by performing a side-to-side anastomosis of the CA and EJV on the right side of the neck of the swine. Flow from the right carotid proximal to the anastomosis is clamped off. Therefore, the flow from the left carotid enters the left RM and flows to the right RM as a retrograde flow. The flow then reaches the anastomosis where the blood is transferred into the EJV, completing the flow loop.

Animal protocols are already approved at ASU and at the Barrow Neurological Institute. After appropriate sedation, the animal is placed under general endotracheal anesthesia. A 10 cm incision is made on the right side of the neck. Approximately 5 cm of the CA and the EJV are exposed. Both vessels are clamped at each exposed end and a 2 cm long incision is made along both the CA and EJV. An anastomosis is then performed. The CA is then ligated 1 cm proximal to the anastomosis in order to divert blood flow into the EJV. Next, the distal external carotid is followed up to the base of the skull at the branch of the AP vessel. The carotid distal of the branch is ligated and electrocoagulated. The right occipital artery and the muscular branch of the AP artery are then also occluded by ligation and electrocoagulation. The incision is closed and the animal is awakened and allowed to recover for at least 48 hours to allow the peripheral cerebrovasculature to accommodate the sudden change in blood flow to the brain.

After a recovery period, the swine are again sedated and catheterized via femoral artery access. A single lumen catheter is placed via fluoroscopic x-ray guidance (angiography) into the left AP artery near the RM. The catheter will allow injection of the polymer into the RM and AP as described below.

The materials used to form the embolus were poly(propylene glycol) diacrylate (Mw 900) (PPODA), pentaerithrytol tetrakis 3-merkaptopropenate (QT), Conray™ (an aqueous radioactive tracing compound), and 5 N NaOH. Initially, it was necessary to titrate the Conray™ to a pH of 11.6 using a small amount of the NaOH. After this titration is complete, all of the precursors were filtered with 0.2 μm filters to ensure their sterility. This increased pH acted as a control upon the speed of the reaction and helped to determine the rate at which the polymer gelled. After preparing the aqueous carrier/tracing solution, 0.45 g of QT, 1.657 g of PPODA, and 0.702 g of Conray™ were loaded into separate sterile syringes under sterile conditions. At this point, the mixture was up to 24 hours before the procedure is to take place.

For the implantation procedure, the utilization of a stainless steel syringe and syringe pump was necessary. At the procedure, the PPODA and QT were loaded into a stainless steel syringe. When the surgeon was prepared for the injection of the material, the modified Conray™ was introduced to the system. This introduction involved employing a syringe junction to push the Conray™ into the stainless steel syringe from its original sterile syringe. These joined syringes were then be used to mix the precursors mechanically at roughly 1 Hz for two minutes. At the end of the mixing process, the metal syringe was left full up to the mark on the shaft (corresponding to roughly 1.7 mL of fluid). Once the correct volume of precursors is loaded, the stainless steel syringe was attached to a Cooke™ catheter, and the pump was engaged at 2:30.

As shown in FIG. 8B, this pre-gelled material (1.7 mL) is then injected from a single-lumen microcatheter from the left AP artery of the left carotid artery (CA) using a stainless steel syringe and a syringe pump 2.5 minutes after beginning the mixing procedure. The polymer injection (300 uL) is controlled into the AP and RM so that the RM is occluded, but the circle of Willis (CW) remains open and able to supply blood to the brain. Within the RM and distal portion of the AP artery the material solidifies. Laboratory tests have shown a complete injection of the targeted amount of material following this procedure at roughly 4:00. Once the material was injected, the catheter was left in place for another 4:00 to ensure the polymer was fully gelled, and then the catheter was gently rotated and removed to prevent any possibility of stranding.

Angiography is used during and after injection to assess the extent of polymerization, occlusion, and blood flow redistribution. After injection, the swine is awakened to survive. A second angiogram is performed at the end of the 3 month swine survival and immediately before sacrifice.

After embolization of the AVM model, the animal is observed for any abnormalities and clinical sequelae. The animals are sacrificed and histological analysis performed after 3 months. The swine are perfused and the polymerized vessel samples tested for mechanical stability and tissue reactivity. Brain and rete tissue are fixed in 10% buffered formalin, sectioned on a cryotome and then stained with hematoxalin and eosin.

Figure 9:
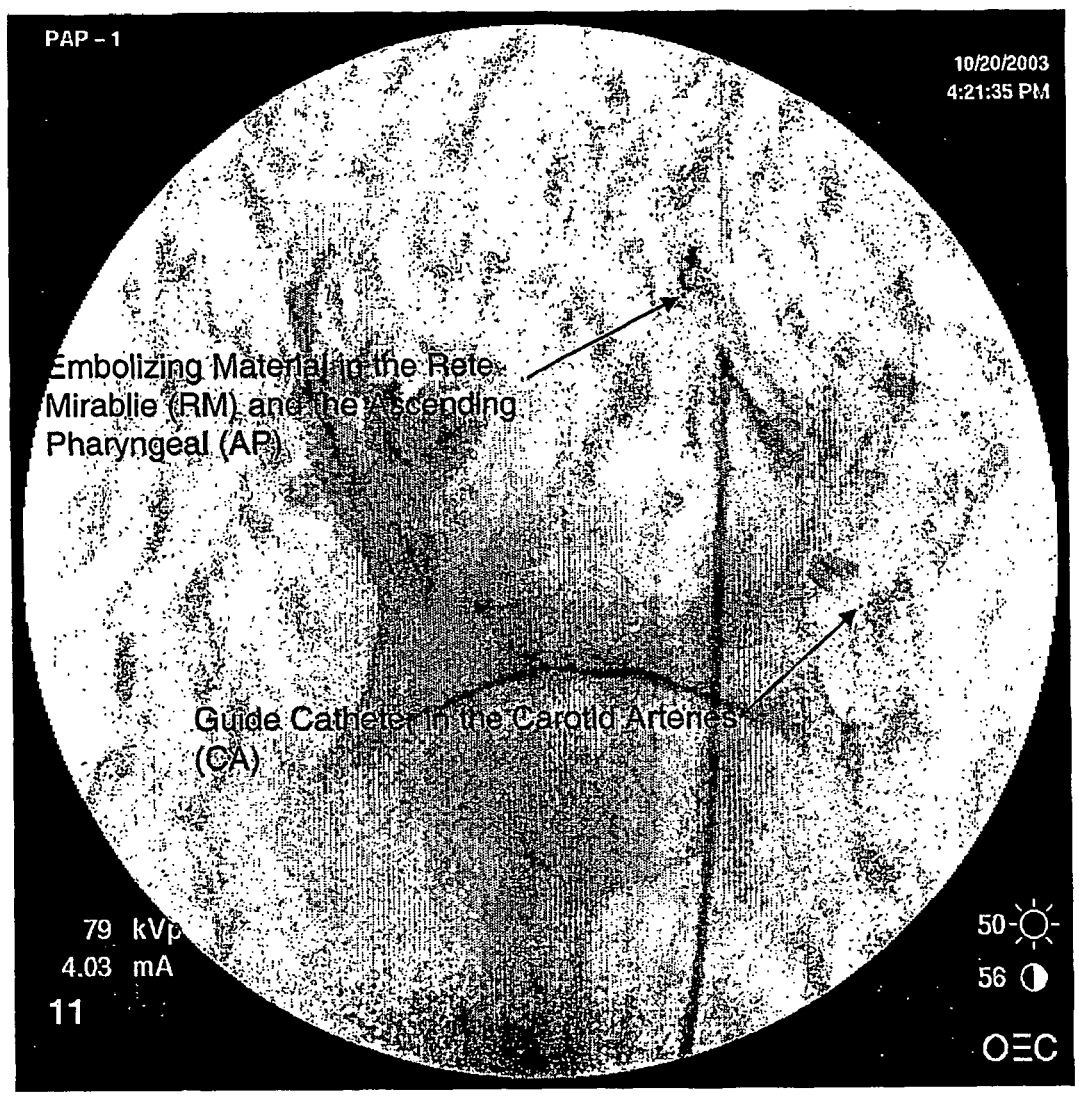
FIG. 9, fluoroscopic image taken just after delivery of a PPODA/QT material into the Rete Mirabile (RM) and Ascending Pharyngeal (AP) showing successful embolized.

Previous partial occlusion injections and previous swine survival verified the technique is indeed feasible and effective. After polymer injection, swine survived in normal health, without induced neurological deficits as a result of the embolization. For example, FIG. 9 shows a fluoroscopic image taken just after delivery of a PPODA/QT material into the Rete Mirabile (RM) and Ascending Pharyngeal (AP). As shown in the fluoroscopic image the material has successfully embolized the RM of the swine and ascending pharyngeal of the swine.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the compositions and methodologies that are described in the publications, which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

While this invention has been described in detail with reference to a certain preferred embodiments, it should be appreciated that the present invention is not limited to those precise embodiments. Rather, in view of the present disclosure that describes the current best mode for practicing the invention, many modifications and variations would present themselves to those of skill in the art without departing from the scope and spirit of this invention. In particular, it is to be understood that this invention is not limited to the particular methodology, protocols, cell lines, animal species or genera, constructs, and reagents described as such may vary, as will be appreciated by one of skill in the art. The scope of the invention is, therefore, indicated by the following claims rather than by the foregoing description. All changes, modifications, and variations coming within the meaning and range of equivalency of the claims are to be considered within their scope.

What is claimed is:

1. A method of embolizing a blood vessel or vascular malformation, comprising:
   blocking blood flow in a blood vessel;
   administering to the blood vessel or vascular malformation a composition comprising a nucleophilic component including pentaerythritol-tetrakis(3-mercaptopropionate) (QT) and a component containing a conjugated unsaturated bond including poly(propylene glycol)diacrylate; and
   crosslinking, within the blood vessel or vascular malformation, the nucleophilic component with the component containing a conjugated unsaturated bond so as to form a crosslinked emboli and occlude the blood vessel or vascular malformation.

2. The method of claim 1 wherein the composition further comprises a buffer solution.

3. The method of claim 2 wherein the buffer is a phosphate buffer.

4. The method of claim 1 wherein the composition further comprises a surfactant.

5. The method of claim 1 wherein the composition further comprises a base.

6. The method of claim 5 wherein the base is NaOH.

7. The method of claim 1 wherein the composition gels within the blood vessel within 30 minutes of introduction.

8. The method of claim 1 wherein the composition gels within the blood vessel within 15 minutes of introduction.

9. The method of claim 1 wherein the composition further comprises at least one additional agent selected from the group consisting of radiopaque agents and nonsteroidal anti-inflammatory compounds.

10. The method of claim 1 further comprising a second thiole precursor.

11. The method of claim 10 wherein the second thiole precursor is dithiothreitol (DTT).

12. The method of claim 1 wherein the component containing a conjugated unsaturated bond consists of polypropylene glycol diacrylate (PPODA).

13. The method of claim 1 wherein the component containing a conjugated unsaturated bond further includes polyethylene glycol diacrylate (PEGDA).

14. The method of claim 1 wherein the component containing a conjugated unsaturated bond further includes pentaerythritol triacrylate (TA).

15. The method according to claim 1 further comprising increasing the pH of the composition prior to introducing the composition.

16. The method according to claim 1 wherein the composition is introduced into the blood vessel through a catheter.

17. The method according to claim 16 wherein the catheter is a balloon catheter.

18. The method according to claim 1 wherein the blood vessel for embolization has an arteriovenous malformation.

* * * * *